US008062651B1

(12) United States Patent  
Zhang et al.

(10) Patent No.: US 8,062,651 B1
(45) Date of Patent: Nov. 22, 2011

(54) **ATTRACTANT PHEROMONE FOR THE MALE PINK HIBISCUS MEALYBUG, *MACONELLICOCCUS HIRSUTUS* (GREEN) (HOMOPTERA: PSEUDOCOCCIDAE)**

(75) Inventors: Aijun Zhang, Silver Spring, MD (US); James E. Oliver, Laurel, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1721 days.

(21) Appl. No.: 11/080,892

(22) Filed: Mar. 14, 2005

Related U.S. Application Data

(60) Provisional application No. 60/553,421, filed on Mar. 16, 2004.

(51) Int. Cl.
*A01N 25/00* (2006.01)
*A01N 25/08* (2006.01)
*A01N 25/32* (2006.01)
*A01N 37/08* (2006.01)
*C07C 67/02* (2006.01)

(52) U.S. Cl. ........ 424/405; 424/406; 424/409; 514/572; 560/261

(58) Field of Classification Search .................. 560/261; 424/84, 405, 406, 409; 514/572
See application file for complete search history.

(56) References Cited

U.S. PATENT DOCUMENTS

| 3,131,234 | A | * | 4/1964 | Martin | 585/604 |
| 3,700,717 | A | | 10/1972 | Kappeler et al. | |
| 3,781,333 | A | | 12/1973 | Kappeler et al. | |
| 3,860,669 | A | * | 1/1975 | Blume | 585/16 |
| 3,912,702 | A | * | 10/1975 | Blume | 526/336 |

(Continued)

OTHER PUBLICATIONS

Chibiryaev et al., DN 116:59006, HCAPLUS, abstract of Zhurnal Organicheskoi Khimii (1991), 27(6), 1909-13.*

(Continued)

*Primary Examiner* — Sabiha Qazi
(74) *Attorney, Agent, or Firm* — John D. Fado; G. Byron Stover

(57) ABSTRACT

A composition for attracting male pink hibiscus mealybugs which contains a carrier material or carrier and effective amount of (R)-lavandulyl (S)-2-methylbutanoate and (R)-maconelliyl (S)-2-methylbutanoate. Also a method for attracting male pink hibiscus mealybugs to an object or area, which method involves treating said object or area with effective amount of (R)-lavandulyl (S)-2-methylbutanoate and (R)-maconelliyl (S)-2-methylbutanoate. Cyclobutanes, 2,2-dimethyl-3-(1-methylethylidene)cyclobutanes, having the formula:

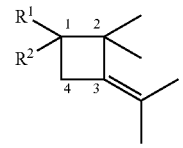

wherein $R^1$ is hydrogen, a $C_{1-11}$ straight or branched alcohol, aldehyde, alkyl, ether (e.g. methanol, ethanal, 4-methylhexane, heptyloxymethane), or esters thereof with a $C_{1-10}$ saturated or unsaturated, straight or branched acid (e.g., formic acid, acetic acid, 2-methylbutyric acid, 3-methyl-2-butenoic acid) and $R^2$ is hydrogen, methyl, $C_{1-10}$ saturated or unsaturated, straight or branched alkyl (e.g. hexane, isopropenyl, 4-methyl-4-pentene). A method of disrupting male pink hibiscus mealybug mating with female pink hibiscus mealybugs, involving exposing a pink hibiscus mealybug population to a composition containing a pink hibiscus mealybug mating disrupting effective amount of (R)-lavandulyl (S)-2-methylbutanoate and (R)-maconelliyl (S)-2-methylbutanoate, and optionally a carrier material or carrier.

9 Claims, 14 Drawing Sheets

U.S. PATENT DOCUMENTS

| | | | | |
|---|---|---|---|---|
| 4,578,484 | A | * | 3/1986 | Skattebol et al. ............. 549/360 |
| 4,584,193 | A | * | 4/1986 | Burkholder et al. ............ 424/84 |
| 5,250,566 | A | * | 10/1993 | Nair .............................. 514/459 |
| 5,714,139 | A | * | 2/1998 | Eller .............................. 424/84 |
| 6,054,141 | A | * | 4/2000 | Mayer et al. ................... 424/405 |
| 6,504,058 | B1 | * | 1/2003 | Basarab et al. ............... 564/189 |
| 6,532,780 | B1 | * | 3/2003 | Frantz ............................ 70/225 |

OTHER PUBLICATIONS

Garret et al., DN 112:157971, HCAPLUS, abstract of J. of Organic Chem. (1990), 55(6), 1909-15.*

Rao et al., DN 108:111681, HCAPLUS, abstract of J. of Organic Chem. (1988), 53(4), 745-51.*

Eierdanz, Horst et al. (DN 101:71904, CAPLUS, abstract of Angewndte Chemie (1984), 96(7), 513-514).*

Krebs, Adolf et al. (DN 100:120557 , HCAPLUS, abstract of Chemische Berichte (1984), 117(1), 277-309).*

Dai, Sheng-Hong et al., DN 76:139676, HCAPLUS, abstract of J. of org. Chemistry (1972), 37(7), 950-5).*

Krebs, Adolf et al. (DN 100:84932, HCAPLUS, abstract of Chemische Berichte (1984), 117(1), 310-21).*

Chibiryaev, A. M. et al., DN 116:59006, HCAPLUS, abstract of Zhurnal Organicheskoi Khimii (1991), 27(6), 1209-13).*

Erickson, H.K., et al., "Chrysanthemyl Diphosphate Synthase. The Relationship Among Chain Branching, and Cyclopropanation Reactions in the Isoprenoid Biosynthetic Pathway", J. Am. vol. 125, pp. 6886-6888, 2003.

Zhang, Aijun, et al., "Sex pheromone of the pink hibiscus mealybug, Maconellicoccus hirsutus contains an unusual cyclobutanoid monoterpene," PNAS, Jun. 29, 2004, vol. 101, No. 26, pp. 9601-9606.

Zhang, Aijun, et al., "Sex Pheromone of the female Pink Hibiscus Mealybug, Maconellicoccus irsutus (Green) (Homopters: Pseudococcidae): Biological Activity Evaluation," Environmental Entomology , Apr. 2005, vol. 34, No. 2, pp. 264-270.

Zhang, Aijun, et al., "Enantioselective Synthesis of the Female Sex Pheromone of the Pink Hibiscus Mealybug, Maconellicoccus hirsutus," Journal of Agricultural and Food Chemistry, 2005, vol. 53, No. 7, pp. 2451-2455.

Zhang, Aijun, et al., "Chiral synthesis of maconelliol: a novel cyclobutanoid terpene alcohol from pink hibiscus mealybug, Maconellicoccus hirsutus," Science Direct, 2004, vol. 45, pp. 9401-9403.

Shirali, Shyam, et al., "Enantioselective Synthesis of (R)-2-Methyalalkanoic Acids: A Convenient Approach to -Substituted Chiral Carboxylic Acid Derivatives," Synthetic Communications, 2004, vol. 34, No. 18, pp. 3435-3441.

Bloor, Stephen, "Raoulic acid A Novel Bioactive C Terpene Acid from Raoulia Australis," Tetrahedron Letters, 1993, vol. 34, No. 35, pp. 5617-5620.

Arai, Tomonori, et al., "Identification of a Sex Pheromone Component of Pseudococcus cryptus," Journal of Chemical Ecology , Oct. 2003, vol. 29, No. 10, pp. 2213-2223.

Bierl-Leonhardt, Barbara A., et al., "Isolation, Identification, and Synthesis of the Sex Pheromone of the Citrus Mealybug, Planococcus Citri (Risso)," Tetrahedron Letters, 1981, vol. 22, pp. 389-392.

Phillips, Thomas W., et al., "Aggregation Pheromone of the Deodar Weevil, Pissodes nemorensis (Coleoptera: Curculionidae): Isolation, and Activity of Grandisol and Grandisal," Journal of Chemical Ecology , 1984.

Hedin, Paul A. et al., "Identification of Male Pecan Weevil Pheromone," Journal of Chemical Ecology, 1997, vol. 23, No. 4, pp. 965-977.

Francke, Wittko, et al., "Terpenoids from bark beetles, solitary bees and danaine butterflies," Pure & Appl. Chem., 1989, vol. 61, No. 3, pp. 539-542.

Bier-leonhardt, Barbara A., et al., "Identification of the Pheromone of the Comstock Mealybug," Life Sciences, vol. 27, pp. 399-402.

Bier-Leonhardt, B. A., et al., "Isolation, Identification Synthesis, and Bioassay of the Pheromone on the Comstock Mealybug and some Analogs," Journal of Chemical Ecology, 1982, vol. 8, No. 4, pp. 689-699.

Williams, D.J., "A Brief account of the hibiscus mealybug Maconelliococcus hirsutus (Hemiptera Pseudococcidae), a Pest of Agriculture and Horticulture, with Descriptions of two Related Species from Southern Asia," Bulletin of Entomological Research, vol. 86, pp. 617-628.

Hara, A.H., "Finding Alternative Ways to Control Alien Pests- Part 2: New Insecticides introduced to Fight Old Pests," Official Publication of the Landscape Industry Council of Hawaii, Jan./Feb. 2000, vol. 4, No. 1 pp. 5.

Serrano, Miguel S., et al., "Attraction of Males by Virgin Females of the Mealybug Maconellicoccus hirsutus (Hemiptera: Pseudococcidae)," Enviromental Entomology, 2001, vol. 30, No. 2, pp. 339-345.

Goolsby, John A., et al., "Seasonal phenology and Natural Enemies of Maconelliococcus hirsutus ( Hemiptera: Pseudococcidae) in Australia," Florida Entomologist, Sep. 2002, vol. 85, No. 3, pp. 494-498.

Zada, A., et al., "Sex Pheromone of the Citrus Mealybug Planococcus citri: Synthesis And Optimiztion of Trap Parameters," Journal of Economic Entomology, 2004, vol. 97, No. 2, pp. 361-368.

Kario, Moses T.K., et al., "Biological control of the hibiscus mealybug, Maconellicoccus hirsutus Green (Hemiptera: Pseudococcidae) in the Caribbean," Integrated Pest Management Reviews, 2000, vol. 5, pp. 241-254.

Petschen, Ines, et al., "First Total Synthesis of the Sex Pheromone of the Oleander Scale Aspidiotus nerii: An Unusual Sesquiterpenic Functionalized Cyclobutane," Chem. Eur. J., 1999, vol. 5, No. 11, pp. 3299-3309.

Millar, Jocelyn G., et al., "Developmental and Optimization of Methods for Using Sex Pheromone for Monitoring the Mealybug Planococcus ficus (Homoptera: Pseudococcidae) in California Vineyards," Journal of Economic Entomology, 2002, vol. 95, No. 4, pp. 706-714.

Bohlmann, Ferdinand, et al., "Types of Sesquiterpenes from Arternisia Douglasians," Phytochemistry, 1982, vol. 21, No. 11, pp. 2691-2697.

Norte, Manuel, et al., "Viridianol, a Rearranged Sesquiterpene with a Novel Carbon Skeleton from Laurencia viridis," Tetrahedron Letters, 1994, vol. 35, No. 26, pp. 4607-4610.

Serrano, Miguel S., et al., "Evaluation of Host Plants and a Meridic Diet for Rearing Maconellicoccus Hirsutus (Hemiptera: Pseudococcidae) and its Parasitoid Anagyrus Kamali (Hymenoptera: Encryrtidae)," Florida Entomologist, Sep. 2002, vol. 85, No. 3, pp. 417-4257.

Hinkley, Simon F. R., et al., "Alcohol from Juniperus oxycedrus is Reassigned as 15-Hydroxy-B-caryophyllene," Tetrahedron Letters, 1994, vol. 35, No. 22, pp. 3775-3776.

Tumlinson, J. H., et al., "Sex Pheromones Produced by Male Boll Weevil: Isolation, Identification, and Synthesis," Science, Nov. 21, 1969, vol. 166, pp. 1010-1012.

Francke, W., "Convergency and Diversity in Multicomponent Insect Pheromones," Elsevier Science Publishers, 1986, pp. 327-336.

Booth, Donald C., et al., "Aggregation Pheromone Components of Two Species of Pissodes Weevils (Coleoptera: Curculionidae): Isolation, Identification, and Field Activity," Journal of Chemical Ecology, 1983, vol. 9, No. 1, pp. 1-12.

Einhorn, Jacques, et al., "Sex pheromone of the oleander scale, Aspidiotus nerii: Structural characterization and absolute configuration of an unusual functionalized cyclobutane," Biochemistry, Aug. 1998, vol. 95, pp. 9867-9872.

* cited by examiner

1

2

D

E

7b → 1c SS + 1d SR

ATTRACTANT PHEROMONE FOR THE MALE PINK HIBISCUS MEALYBUG, *MACONELLICOCCUS HIRSUTUS* (GREEN) (HOMOPTERA: PSEUDOCOCCIDAE)

REFERENCE TO RELATED APPLICATION

This application claims the benefit of U.S. Provisional Application No. 60/553,421, filed 16 Mar. 2004, which is incorporated herein by reference in its entirety.

BACKGROUND OF THE INVENTION

The present invention relates to a composition for attracting male pink hibiscus mealybug (PHM), which composition contains a male pink hibiscus mealybug attracting effective amount of (R)-lavandulyl (S)-2-methylbutanoate and (R)-maconelliyl (S)-2-methylbutanoate, and optionally a carrier material or carrier. The present invention also relates to a method for attracting male pink hibiscus mealybugs to an object or area, which method involves treating said object or area with a male pink hibiscus mealybug attracting composition containing a male pink hibiscus mealybug attracting effective amount of (R)-lavandulyl (S)-2-methylbutanoate and (R)-maconelliyl (S)-2-methylbutanoate, and optionally a carrier material or carrier. In addition, the present invention relates to a method for disrupting male pink hibiscus mealybugs mating with female pink hibiscus mealybugs, involving exposing a pink hibiscus mealybugs population to a composition containing (R)-lavandulyl (S)-2-methylbutanoate and (R)-maconelliyl (S)-2-methylbutanoate in a quantity sufficient to disrupt male pink hibiscus mealybugs mating with female pink hibiscus mealybugs, and optionally a carrier material or carrier. Furthermore, the present invention relates to a cyclobutane having the formula:

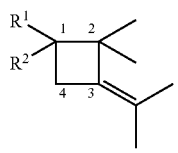

wherein $R^1$ is hydrogen, a $C_{1-11}$ straight or branched alcohol, aldehyde, alkyl, ether (e.g. methanol, ethanal, 4-methylhexane, heptyloxymethane), or esters thereof with a $C_{1-10}$ saturated or unsaturated, straight or branched acid (e.g., formic acid, acetic acid, 2-methylbutyric acid, 3-methyl-2-butenoic acid) and $R^2$ is hydrogen, methyl, $C_{2-10}$ saturated or unsaturated, straight or branched alkyl (e.g. hexane, isopropenyl, 4-methyl-4-pentene).

The pink hibiscus mealybug, *Maconellicoccus hirsutus* (Green) (*Homoptera*: Pseudococcidae), causes severe economic problems throughout tropical and subtropical regions. It appears to be native to Australia or Southern Asia (Williams, D. J., Bull. Entomol., Res. 86: 617-628 (1996)). This exotic insect pest has been spreading through the entire Caribbean region since it was first detected on the island of Grenada in 1994 (Matile-Ferrero, D., and J. Eitienne, Revue Francaise d'Entomologie, 18: 38 (1996); Etienne, J., et al., Bulletin de la Societe entomologique de France, 103: 173-174 (1998)). Since then, it has spread to Southern California, Mexico, Central America, and, in 2002, to Florida (Anonymous, Pink Hibiscus Mealybug *Maconellicoccus hirsutus* (Green), United States Department of Agriculture, Animal and Plant Health Inspection Service (2002), http://www-.doacs.state.fl.us/pi/enpp/ento/pink.htm).

PHM feeds on a wide range of host plants, inflicting severe damage by injecting toxic saliva into the host plant leading to malformation of fruit, leaves and shoots, stunting of plant growth, and eventual plant death (Kairo, M. T. K., et al., International Pest Management Reviews, 5: 241-254 (2000)). Agricultural crops in the United States expected to be at greatest economic risk to PHM invasion include ornamental crops, vegetable crops, citrus, grapes, avocados, and many other plants (Anonymous, The Hibiscus or Pink Mealybug, United States Department of Agriculture, Animal and Plant Health Inspection Service (1996), http://www.aphis.usda.gov/lpa/pubs/fsheet_faq_notice/fs_phphmealybug.html). Potential losses of $750 million per year have been estimated if the insect cannot be controlled (Carter-Lane, S., and J. Redding, Exotic Parasitic Wasps to Attack Invasive Mealybug in California, United States Department of Agriculture, Animal and Plant Health Inspection Service (1999), http://www.aphis.usda.gov/lpa/news/1999/09/MELBUGCA.HTM).

To date, detection of PHM infestations relies on visual inspection, although live virgin females can be used as an attractant source (Stibick, J. N. L., New pest response guidelines: Pink hibiscus mealybug Maconellicoccus hirsutus, United States Department of Agriculture, Animal and Plant Health Inspection Service (1997); Serrano, M., et al., Environ. Entomol., 30: 339-345 (2001)); however, limited availability and low survivorship of live virgin females made this application impractical. A synthetic pheromone would provide a much more economical, convenient, and useful survey tool. An artificial lure might also enable the development of mass trapping and mating disruption technology for managing this pest, which would complement ongoing biological control eradication efforts in the Caribbean, California, and Florida.

SUMMARY OF THE INVENTION

In accordance with the present invention there is provided a composition for attracting male pink hibiscus mealybugs, which composition contains a male pink hibiscus mealybug attracting effective amount of (R)-lavandulyl (S)-2-methylbutanoate and (R)-maconelliyl (S)-2-methylbutanoate, and optionally a carrier material or carrier.

Also in accordance with the present invention is a method for attracting male pink hibiscus mealybugs to an object or area, which method involves treating said object or area with a male pink hibiscus mealybug attracting composition containing a male pink hibiscus mealybug attracting effective amount of (R)-lavandulyl (S)-2-methylbutanoate and (R)-maconelliyl (S)-2-methylbutanoate, and optionally a carrier material or carrier.

Still in accordance with the present invention is a cyclobutane having the formula:

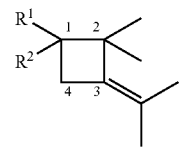

wherein $R^1$ is hydrogen, a $C_{1-11}$ straight or branched alcohol, aldehyde, alkyl, ether (e.g. methanol, ethanal, 4-methylhexane, heptyloxymethane), or esters thereof with a $C_{1-10}$ saturated or unsaturated, straight or branched acid (e.g., formic acid, acetic acid, 2-methylbutyric acid, 3-methyl-2-butenoic acid) and $R^2$ is hydrogen, methyl, $C_{2-10}$ saturated or unsaturated, straight or branched alkyl (e.g. hexane, isopropenyl, 4-methyl-4-pentene).

Also in accordance with the present invention is a composition containing at least one cyclobutane having the formula:

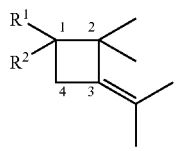

wherein $R^1$ is hydrogen, a $C_{1-11}$ straight or branched alcohol, aldehyde, alkyl, ether, or esters thereof with a $C_{1-10}$ saturated or unsaturated, straight or branched acid and $R^2$ is hydrogen, methyl, or $C_{2-10}$ saturated or unsaturated, straight or branched alkyl; optionally (R)-lavandulyl (S)-2-methylbutanoate, and optionally a carrier material or carrier; preferably one of the cyclobutanes is (R)-maconelliyl (S)-2-methylbutanoate.

Also in accordance with the present invention is a method of disrupting male pink hibiscus mealybugs mating with female pink hibiscus mealybugs, involving exposing a pink hibiscus mealybug population to a composition containing a pink hibiscus mealybug mating disrupting effective amount of (R)-lavandulyl (S)-2-methylbutanoate and (R)-maconelliyl (S)-2-methylbutanoate, and optionally a carrier material or carrier.

DETAILED DESCRIPTION OF THE INVENTION

Figure 1:
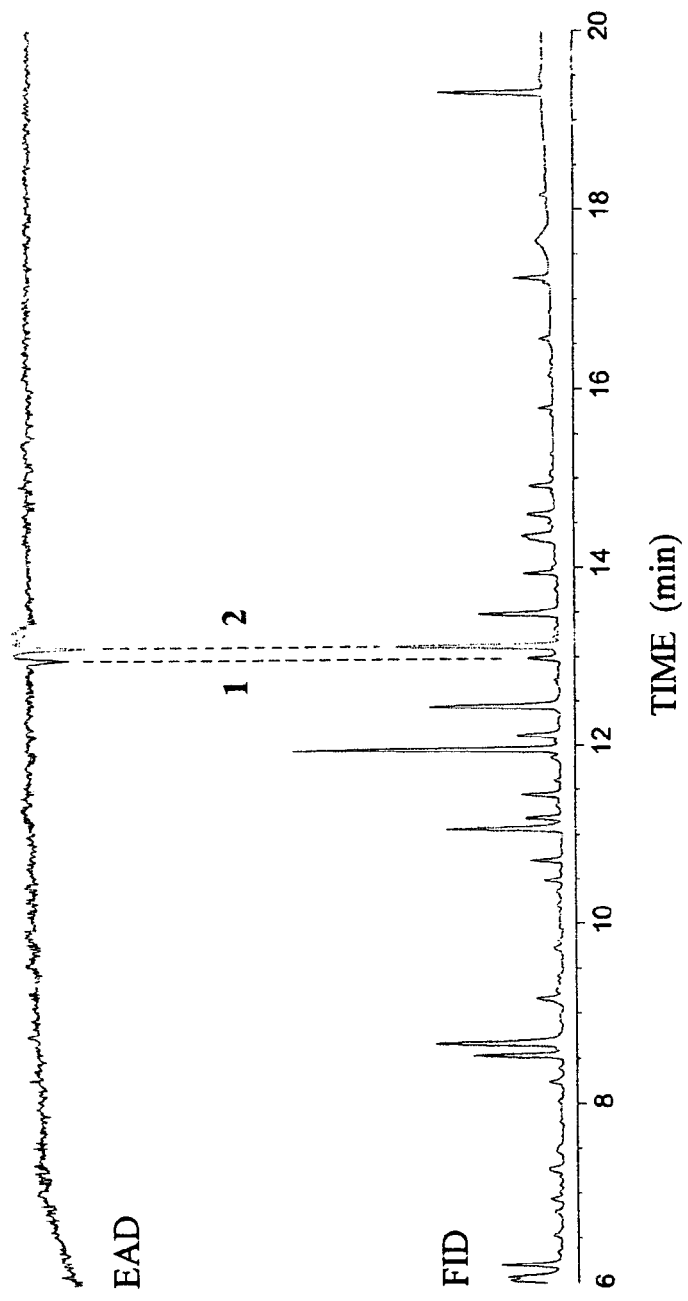
FIG. 1 shows simultaneous responses of flame ionization detection (FID) and EAD of an adult male M. hirsutus to the volatiles of female PHM on a DB-WAXETR capillary column (two EAD active compounds were marked as "1" and "2").

A composition is disclosed for attracting male pink hibiscus mealybugs, which composition contains a male pink hibiscus mealybug attracting effective amount of (R)-lavandulyl (S)-2-methylbutanoate and (R)-maconelliyl (S)-2-methylbutanoate, and optionally a carrier material or carrier. In addition, a method is disclosed for attracting male pink hibiscus mealybugs to an object or area, which method involves treating said object or area with a male pink hibiscus mealybug attracting composition containing a male pink hibiscus mealybug attracting effective amount of (R)-lavandulyl (S)-2-methylbutanoate and (R)-maconelliyl (S)-2-methylbutanoate, and optionally a carrier material or carrier.

Also disclosed are cyclobutanes having the formula:

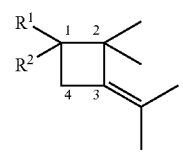

wherein $R^1$ is hydrogen, a $C_{1-11}$ straight or branched alcohol, aldehyde, alkyl, ether (e.g. methanol, ethanal, 4-methylhexane, heptyloxymethane), or esters thereof with a $C_{1-10}$ saturated or unsaturated, straight or branched acid (e.g., formic acid, acetic acid, 2-methylbutyric acid, 3-methyl-2-butenoic acid) and $R^2$ is hydrogen, methyl, $C_{2-10}$ saturated or unsaturated, straight or branched alkyl (e.g. hexane, isopropenyl, 4-methyl-4-pentene). Preferably, $R^1$ is methyl pantanoate and $R^2$ is hydrogen, more preferably $R^1$ is methyl 2-methylbutanoate and $R^2$ is hydrogen (the major pheromone component (R)-maconelliyl (S)-2-methylbutanoate).

The maconelliyl 2-methylbutanoates are made by a method including the steps of: forming verbenone by oxidation of alpha-pinene, generating pinononic acid by oxidative cleavage of the double bond of verbenone, creating tertiary alcohol by Grignard alkylation of the ketone group in pinononic acid, cyclization to form a lactone, elimination to form an unsaturated isopropenyl group on the ring, reduction of acid group to form alcohol, and esterification of said alcohol to form a maconelliyl 2-methylbutanoate according to the present invention.

The attractant of the present invention may be applied with a carrier component or carrier (e.g., agronomically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insect attractants in general and are well known in the art. All of these substrates have been used to release insect attractants in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, cellulosic and rubber materials and synthetic polymers.

The amount of attractant used will be at least an effective amount. The term "effective amount," as used herein, means the minimum amount of attractant needed to attract the male pink hibiscus mealybug to a treated area or object when compared to the same area or object which is untreated. Preferably the molar ratio of (R)-lavandulyl (S)-2-methylbutanoate: (R)-maconelliyl (S)-2-methylbutanoate is about 1:about 2 to about 1:about 10 (e.g., 1:2 to 1:10). Preferably the molar ratio is about 1:about 5 (e.g., 1:5). Effective loadings of the attractant in the compositions may vary between about 1 to about 50 (e.g., 1-50) µg/septum for monitoring purpose (preferably about 1-about 30 (e.g., 1-30) µg/septum, more preferably about 10-about 20 (e.g., 10-20) µg/septum). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% of the mealybugs and would be statistically significant in comparison to a control. The attractant composition may or may not contain a control agent for pink hibiscus mealybugs, such as a biological control agent or an insecticide known in the art to kill pink hibiscus mealybugs. Other compounds may be added to the attractant composition provided they do not substantially interfere with the intended activity of the attractant composition; whether or not a compound interferes with attractant activity can be determined, for example, by the procedures utilized below.

The attractant can also be used to disrupt mating within a mealybug population. This is done by exposing a mealybug population to the attractant in a quantity sufficient to cover the pheromone emissions by the female mealybugs and thereby prevent potential mates from finding each other, thus disrupting the ability of the mealybugs to mate. The amount of attractant used will be at least an effective amount. The term "effective amount," as used herein, means the minimum amount of attractant needed to disrupt male pink hibiscus mealybugs mating with female pink hibiscus mealybug. Preferably the molar ratio of (R)-lavandulyl (S)-2-methylbutanoate:(R)-maconelliyl (S)-2-methylbutanoate is about 1:about 2 to about 1:about 10 (e.g., 1:2 to 1:10), more preferably the molar ratio is about 1:about 5 (e.g., 1:5). Effective loadings of the attractant in the compositions may vary between about 100 to about 1000 (e.g., 100-1000) µg/dispenser for mating disruption purpose (preferably about 100-about 800 (e.g., 100-800) µg/dispenser, more preferably about 300-about 500 (e.g., 30-500) µg/dispenser).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Identification of the sex pheromone of the pink hibiscus mealybug, *Maconellicoccus hirsutus* (Green) (*Homoptera*: Pseudococcidae):

Insects Mass-Rearing: Virgin female mealybugs, *M. hirsutus*, were mass-reared on Japanese pumpkins in the USDA-APHIS laboratory in Puerto Rico. The Japanese pumpkins, *Cucurbita moschata* L., were field-grown at the USDA-ARS Experimental Station at St. Croix, U.S. Virgin Islands. Infestations of *M. hirsutus* were achieved by brushing 24-h-old crawlers with a camel's hair brush onto the pumpkins twice a week. Infested pumpkins were maintained in an incubator at 27±1° C., 70% RH, in total darkness. When the first molt occurred, the infested pumpkins were completely submerged for 30 to 40 s in a 100-ppm solution of an insect growth regulator, pyriproxifen (Distance, Valent USA, Walnut Greek, Calif.), which prevents developments of males (Bierl-Leonhardt, B. A., et al., Tetrahedron Lett., 22: 389-392 (1981)). After air-drying for 1 h, pumpkins were placed in male-exclusion cages and kept in a rearing room at 26±2° C., 60+10% RH in darkness. If ovisacs were observed, the treated pumpkins were considered contaminated with mated females, and were rejected for pheromone collection purposes.

Pheromone Collection and Purification: The pheromone was collected using two groups of 14-day-old females (ca. 3000 virgin females per group) in San Juan, Puerto Rico. The females with white flocculent wax filaments were separately brushed into two 1-liter, 4-necked glass containers (Zhang, A., et al., J. Chem. Ecol., 20: 2415-2427 (1994)). Humidified air was drawn into the container through 6-14 mesh activated charcoal (Fisher Scientific, Pittsburgh, Pa.) and out of the container through two traps (15 cm×1.5-cm OD) containing Super Q (200 mg each; Alltech Associates, Inc., Deerfield, Ill.) by vacuum (~1 liter/min). Females were fed with 10% sugar solution on cotton balls and aerated continuously for 47 days at room temperature and 16 L:8 D photoperiod. The adsorbent traps were changed every 5 days and the adsorbents were eluted with methylene chloride (4×0.5 ml/each sample).

The eluates were stored in −30° C. freezer after eluting and then shipped to Beltsville, Md. by an express carrier. Each sample was concentrated to ~100 μl under nitrogen for further analyses. Seven collections were then combined and concentrated. The combined extracts were subjected to either fractionation by micro-preparative gas chromatography (GC) or micro-reaction. The micro-preparative GC fractionation was carried out on a HP 6890 GC equipped with Gerstel preparative fraction collector (Gerstel Inc., Baltimore, Md.) using a 60 m×0.53-mm ID, 0.50-μm film-thickness DB-1 capillary column (J&W Scientific Inc., Folsom, Calif.). Injector temperature was 32° C. at injection and programmed to 230° C. at 60° C./min to transfer solute onto the column which was held at 80° C. for 2 min, then programmed to 220° C. at 30° C./min and held for 30 min. Split ratio of column effluent to FID and fraction collector was set at 4:96. The collector was cooled to −20° C. by circulating MeOH from a benchtop refrigeration unit (Julabo F25-MP, JULABO USA, Inc., Mertztown, Pa.) and the collection efficiency was ca. 70%.

Analytical Methods: The coupled gas chromatographic-electroantennographic detection (GC-EAD) system used was as previously described (Zhang, A., et al., J. Chem. Ecol., 23: 31-245 (1997); Zhang, A., et al., J. Chem. Ecol., 25: 1221-1232 (1999); Zhang, A., and S. Polavarapu, J. Chem. Ecol., 29: 2153-2164 (2003)). A HP 6890 GC equipped with a 60 m×0.25-mm ID, 0.25-μm film-thickness DB-WAXETR (J&W Scientific Inc., Folsom, Calif.) capillary column in the splitless mode with hydrogen (1.4 ml/min) as carrier was used for analysis. The column temperature program was hold at 80° C. for 2 min, then heated to 250° C. at 15° C./min and held for 15 min. Electron impact mass spectrometry (EI mass) was conducted on a HP 6890 GC coupled to a HP 5973 Mass Selective Detector using an a 60 m×0.25-mm ID, 0.25-μm film-thickness DB-WAXETR capillary column at 50° C. for 2 min, then programmed to 230° C. at 15° C./min and held for 15 min or a 30 m×0.25-mm ID, 0.25-μm film-thickness DB-1 capillary column (50° C. for 2 min, then programmed to 300° C. at 15° C./min and held for 15 min) with helium as carrier gas. A 70 eV electron beam was employed for sample ionization. Chemical ionization mass spectrometry (CI mass) spectra were obtained from a Finnigan 4510 GC-MS spectrometer with ammonia ($NH_3$) or with deuteroammonia ($ND_3$) as reagent gases using the same above columns and conditions. GC-Fourier transform infrared (FTIR) spectra were recorded on a HP GC coupled to a Bio-Rad IRD II infrared detector using a 60 m DB-WAXETR capillary column with conditions as described as above. Chiral GC analyses was carried out isothermally at 100° C. (55 cm/sec) on a HP 6890 GC equipped with a 30 m×0.25-mm ID, 0.25-μm film-thickness β-DEX 120 capillary column (Supelco, Inc., Bellefonte, Pa.) in the split mode (100:1) with hydrogen as carrier. NMR spectra were recorded in $C_6D_6$ solution on a Bruker QE Plus spectrometer at 300 MHz for $^1H$. The chemical shifts are expressed in ppm relative to the residual solvent for $^1H(C_6H_6$ at δ 7.15 ppm).

Micro-reactions: A pheromone aeration sample was hydrolyzed by treating a 50 μl (ca. 200 ng pheromone) aliquot of combined extracts with 100 μl of 95% methanol and two drops of 2N NaOH in a 2 ml vial for 1.5 h at room temperature. Water (0.5 ml) was then added and the aqueous phase was extracted with hexane (0.5 ml×2). The combined organic layers were concentrated under nitrogen (neutral part). The aqueous phase was acidified to PH<2 by adding 2N HCl and extracted with hexane (0.5 ml×2). The combined organic layers were concentrated under a stream of nitrogen to ca. 50 μl (acid fraction).

Micro-hydrogenation was carried out by a catalytic amount of 10% palladium on carbon (Pd—C, Aldrich, Milwaukee, Wis.) in a 2 ml vial, which was sealed by a hydrogen-filled balloon. Samples included 50 μl of concentrated pheromone extract, hydrolyzed alcohol, and silanized alcohol (ca. 100 ng/each). Each sample was diluted with 100 μl ethyl acetate and stirred with a micro magnetic stirrer bar for 10 min. The solution was then transferred to another vial by a micropipette and the reaction vial was washed with 50 μl hexane several times. The resulting organic solution was concentrated to ca. 20 μl.

Micro-silylation of hydrolyzed alcohols were performed in 1 ml vials: An aliquot containing ca. 50 ng of hydrolyzed or hydrogenated alcohol solution was evaporated to near dryness and the residue was redissolved in 20 μl of silylation reagent, N,O-bis(trimethysily)trifluoroacetamide (BSTFA, Aldrich, Milwaukee, Wis.). The reaction vial was maintained at 65° C. for 2 h and excess reagent was evaporated by nitrogen, a few drops of hexane were added, the solvent was again evaporated, and the sample was redissolved in ca. 10 μl hexane.

Field Bioassays: Gray halo-butyl rubber septa (5 mm, West Pharmaceutical Services, Kearney, Nebr.) loaded with 1 μg of RS, SR, RR, and SS binary diastereoisomeric mixtures of two candidate pheromone compounds placed on white sticky cards (Pherocon V traps, Trécé, Salinas, Calif.) were used for the field trails in Florida. Treatments were arranged in a randomized complete block design with nine replicates and about ~1 m between traps within replicates. The cards were attached to the top of metal rods and placed one foot above hibiscus plants in a hedgerow. Cards were collected, put separately in transparent plastic bags, and brought back to the laboratory to count the trapped male PHM under a microscope. Comparisons were made between candidate synthetic mixtures and a blank control trap.

Figure 2:
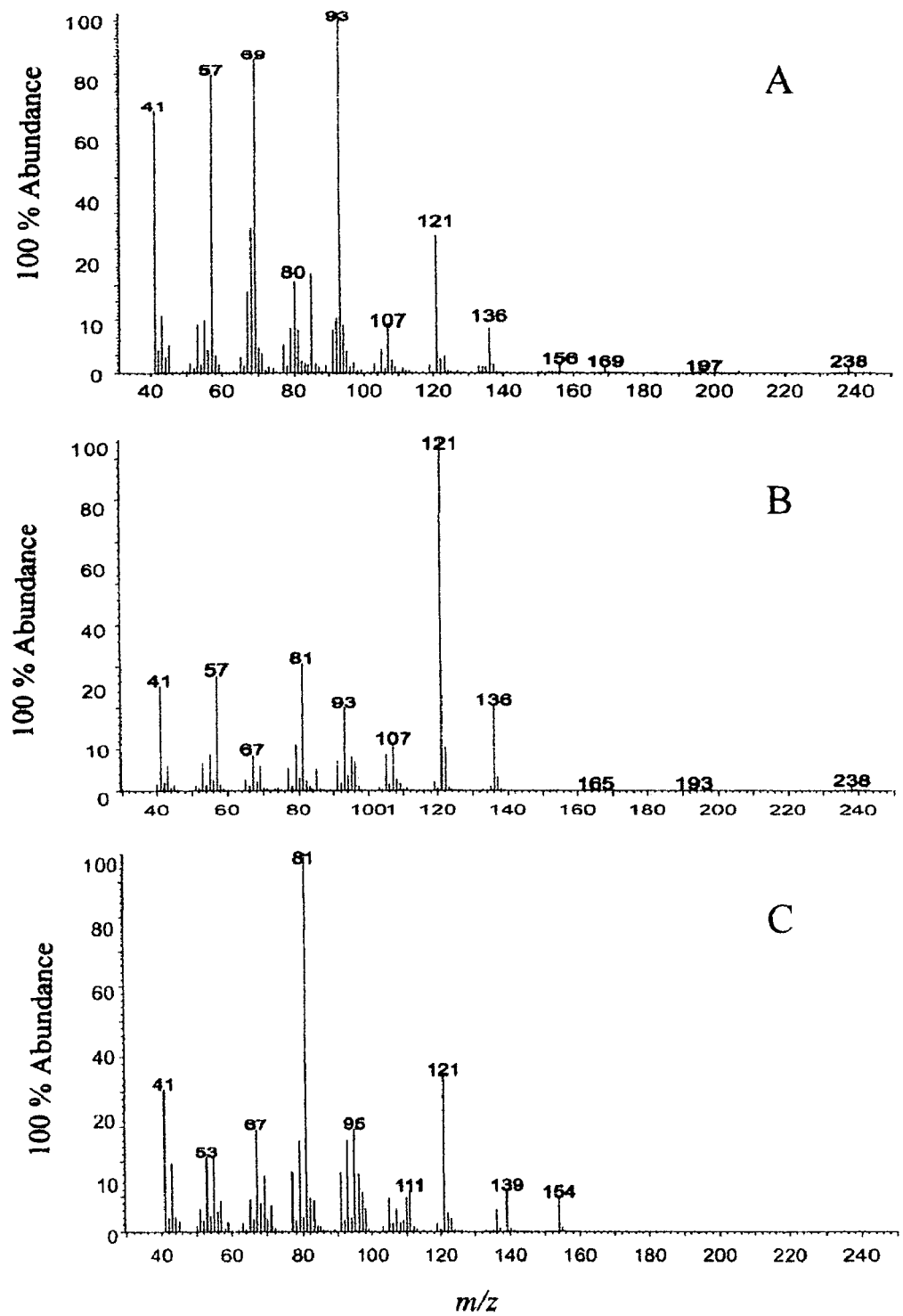
FIG. 2 shows the EI-MS spectra of the natural pheromone and alcohol: (A) compound 1; (B) compound 2; (C) maconelliol.

Results: Coupled GC-EAD analyses of female airborne extracts demonstrated that male *M. hirsutus* antennae consistently responded to two compounds, 1 and 2 (FIG. 1). The EI mass spectra of both compounds (FIG. 2 A, B) contained parent ions at m/z 238. The assumption of m/z 238 as the molecular ion was confirmed by CI mass spectra (relative intensities in parentheses) {m/z 239 ([M+H]$^+$, 25) and 256 ([M+NH$_4$]$^+$, 100) for 1 and 239 ([M+H]$^+$, 28) and 256 ([M+NH$_4$]$^+$, 100) for 2} with ammonia ($NH_3$) as the reagent gas. The corresponding ions (M+2 and M+22) were obtained with deuteroammonia ($ND_3$) indicating that neither compounds contained exchangeable protons. Both compounds produced fragment ions at m/z 136 (M−102) without any other significant fragments in the high-mass region (between m/z 238 and 136, FIGS. 2A and 2B), suggesting that a neutral molecule was easily eliminated during fragmentation. The ions of m/z 136 (M−102) could be interpreted as [M—$C_4H_9$COOH]$^+$ or [M—$C_6H_{13}$OH]$^+$. This hypothesis was supported by GC-FTIR data because 1 and 2 showed strong absorptions at 1747 cm$^{-1}$ (C=O) and hydrocarbon absorption bands but few other features. Thus, both compounds were proposed to be esters of either a $C_5$ acid or a $C_6$ alcohol.

In addition, presence of 2 double bonds in compound 1 and 1 double bond and 1 ring in compound 2 could be deducted from the CI mass ions of compounds produced by catalytic micro-hydrogenation. The ions exhibited at m/z 243 ([M+H]$^+$, 5) and 260 ([M+NH$_4$]$^+$, 100) indicated that 242 was the molecular weight and 4 hydrogens had been added to compound 1. Similarly, ions at m/z 241 ([M+H]$^+$, 3) and 258 ([M+NH$_4$]$^+$, 100) indicated that 240 was the molecular weight and that only 2 hydrogens had been added to the compound 2. Since both compounds initially possessed the same molecular weight, the uptake of only one mole of hydrogen suggested the existence of a ring as the remaining element of unsaturation in compound 2. Moreover, the hydrogenation product of compound 2 produced two GC peaks (3:1 ratio) with indistinguishable spectra, suggesting that the single double bond had been located either in the ring or connected to the ring with other chiral centers existing in the molecule so that the catalytic micro-hydrogenation occurred in favor of one side of molecule and generated a pair of diastereoisomers in different amounts. It was also noticed that these two derivatives underwent distinctly different fragmentations during mass spectrometry, producing ions at m/z M–70 (instead of M–102), resulting in m/z 170 being the highest mass ions of moderate abundance in the spectra. This fragmentation pathway was not observed before hydrogenation.

Alkaline hydrolysis was performed to confirm the existence of an ester. MS of the acid fractions from both compounds closely matched that of a spectrum of 2-methylbutyric acid (Wiley 275 mass spectral database). The MS of the alcohol (neutral fraction) from compound 1 closely matched a spectrum of lavandulol, suggesting that compound 1 was the 2-methylbutyrate of lavandulol ($C_{15}H_{26}O_2$). It seemed reasonable to assume that compound 2 also had the same molecular formula because it contained the same acid moiety and possessed the same molecular weight. A number of other micro-reactions were then performed in order to get more structural information about the remaining unknown alcohol, which we refer as maconelliol (EI mass spectrum, see FIG. 2C). Micro-hydrogenation confirmed the existence of a double bond and a ring in the alcohol. This reaction gave two widely separated GC peaks with the same MS, demonstrating that maconelliol was a cyclic, unsaturated chiral alcohol {M–70 fragmentation [m/z 86 (47)]}. These hydrogenated alcohols were then subjected to trimethylsilylation. The unique M–70 fragmentation [m/z 158 (21)], was observed again from the MS and molecular weights (m/z 228) were confirmed by CI mass [m/z 229 (15), 246 (100)]. In contrast, trimethylsilylation of the natural alcohol (maconelliol) generated only one GC peak, which exhibited a MS similar to that of the natural pheromone 2. Hydrogenation produced two isomers with indistinguishable {EI mass (M=228), CI mass [m/z 229 (15), 246 (100)]}. Thus, maconelliol was proposed to be a monocyclic, monounsaturated alcohol.

Figure 3:
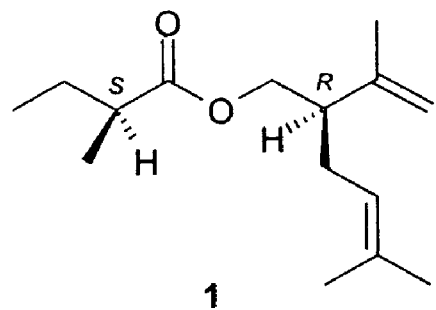
FIG. 3 shows structures of M. hirsutus pheromone components 1, 2 and two tetra-substituted cyclobutane 2-methylbutanoates D and E.
Figure 3:
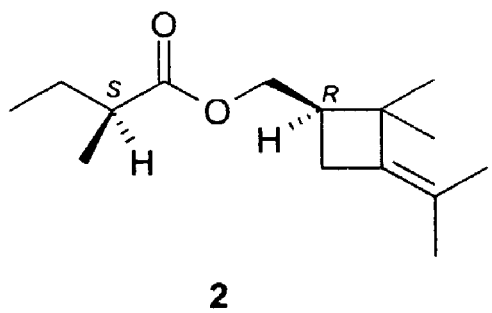
Figure 3:
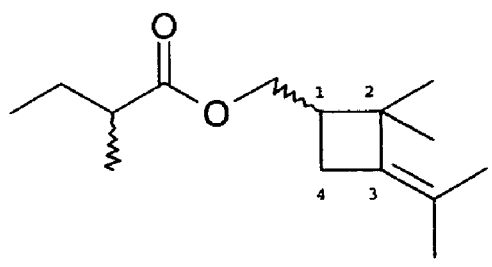
Figure 3:
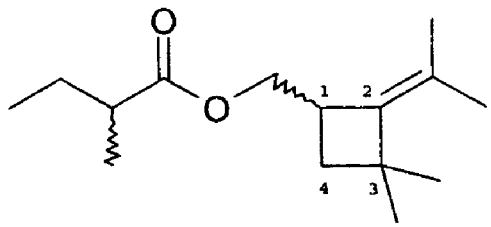

The $^1$H NMR spectrum (FIG. 4) of purified compound 2 (ca. 30-μg obtained by preparative GC) contained resonance for 26 protons including 6 methyl groups, consistent with the assumed molecular formula $C_{15}H_{26}O_2$. A doublet at 4.15 ppm (d, 2H, J=7.57 Hz) corresponded to a methylene in an ester (—O—CH$_2$—CH—). Four distinct methyl signals were clearly displayed; two signals at 1.51 (s, 3H) and 1.40 (s, 3H) ppm from two methyl groups on the double bond (CH$_3$—C=C), and another two signals at 1.24 (s, 3H) and 1.12 (s, 3H) ppm corresponding to a geminal dimethyl [(CH$_3$)$_2$C—] or two methyl groups on quaternary carbons. The remaining two methyl groups supported the presence of a 2-methyl butyrate moiety CH$_3$CH$_2$CH(CH$_3$)CO (δ 0.83, t, 3H, J=7.19 Hz; 1.077, d, 3H, J=6.82 Hz). Accordingly, in the absence of any olefinic protons, the tetra-substituted cyclobutane 2-methylbutanoate (compound D or E, FIG. 3) were considered as reasonable pheromone candidates. The structure D was more consistent with the long-range homoallylic coupling (H—C—C=C—CH) observed for the methylene group in the four member ring. The two protons at the 4 position were not equivalent. Broad signals at δ 2.47 and 2.05 could be interpreted as the homoallylic long-range coupling with the terminal methyl groups on the double bond. Correspondingly, these two methyl groups (δ 1.51 and 1.40) also exhibited the same coupling pattern (coupling constant <1 Hz). This homoallylic long-range coupling was confirmed by $^1$H—$^1$H COSY spectrum and decoupling experiments.

Figure 5:
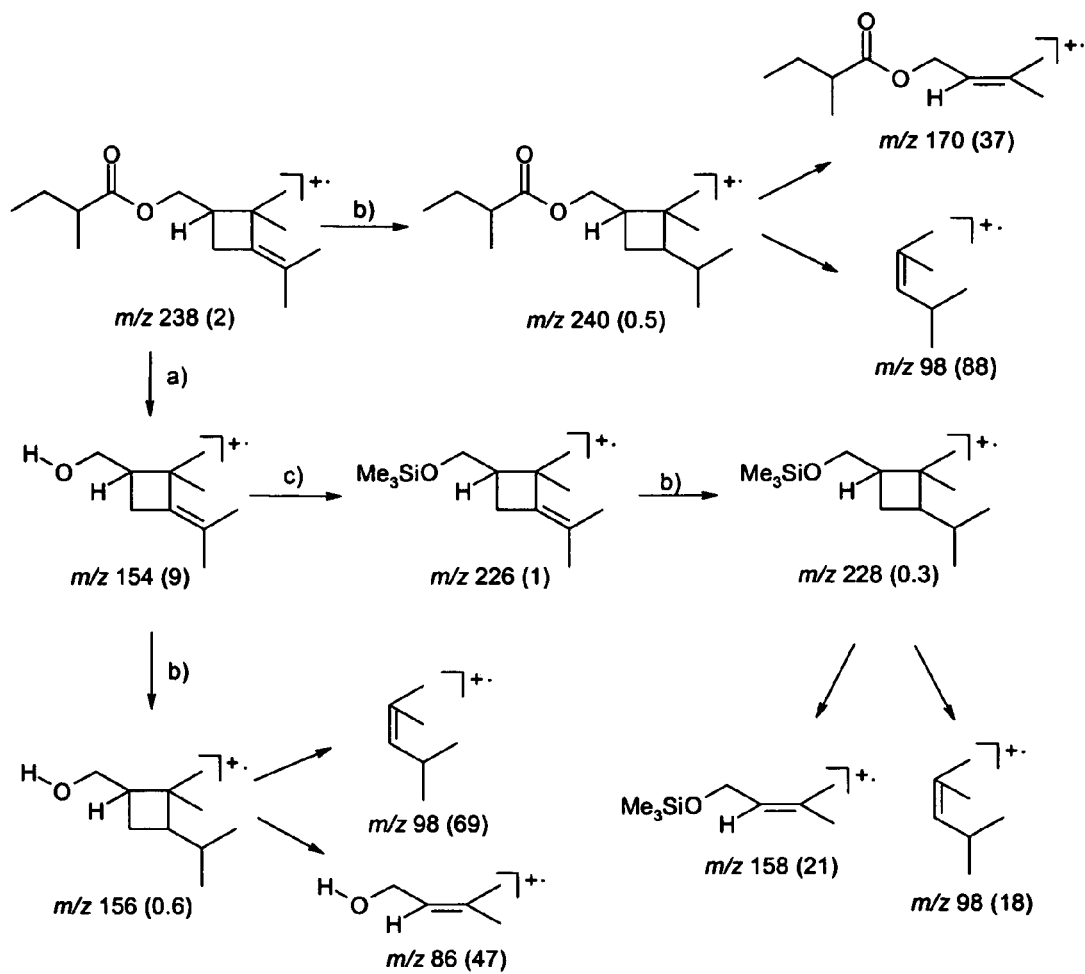
FIG. 5 shows micro-reactions performed on M. hirsutus natural pheromone extracts and possible 2+2 retro-cleavage and major degradation pathway of compound 2 according to EI mass data (relative intensities in parentheses). (a) 2N NaOH in 95% EtOH; (b) H2/Pd—C in EtOAc; (c) BSTFA.

The structure of D was also supported by MS data obtained from products of micro-reactions performed on the natural pheromone. The unique M–70 fragmentation observed in hydrogenated products could be interpreted as a 2+2 retro-cleavage (FIG. 5). The fragment ion, m/z 184 (M–56, $C_4H_8$), would be expected from compound E rather than the ion of m/z 170 (M–70, $C_5H_{10}$). At least two types of 2+2 retro-cleavage ions had been detected in EI mass spectra in all of hydrogenated products. The second type of degradation resulted in an ion at m/z 98. Therefore, the 2+2 retro-cleavage pathway could serve as a diagnostic fragmentation in the characterization of analogues and/or derivatives of the present pheromone. This degradation pathway does not occur with the unsaturated alcohol and alcohol derivative ions because they would have to form unfavorable allene fragments. They instead undergo elimination of a neutral molecule to form the fragment ion, m/z 136 and the daughter ion, m/z 121 (m/z 136–CH$_3$).

In order to confirm the pheromone structure and to define its stereochemistry, all four possible stereoisomers were synthesized for each of compounds 1 and 2. (S)-(+)-2-Methylbutyric acid was commercially available (Aldrich, Milwaukee, Wis.) and (R)-(–)-2-methylbutyric acid was enantioselectively synthesized from (+)-ephedrine hydrochloride and urea (Close, W. J., J. Org. Chem., 15: 1131-1134 (1950); Cardillo, G., et al., J. Org. Chem., 53: 2354-2356 (1988)). (S)-(+)-Lavandulol and (R)-(–)-lavandulol were prepared using the same strategy. (S)-(+)-Maconelliol and (R)-(–)-maconelliol were enantioselectively synthesized from (S)-(–)-α-pinene and (R)-(+)-α-pinene. The synthetic approaches are reported in detail below. The described series of micro-reactions for maconelliol were carried out on the synthetic enantiomer separately. The four diastereoisomers of 1 and 2 produced mass spectra virtually identical to each other and indistinguishable from that of the natural pheromone.

Figure 4:
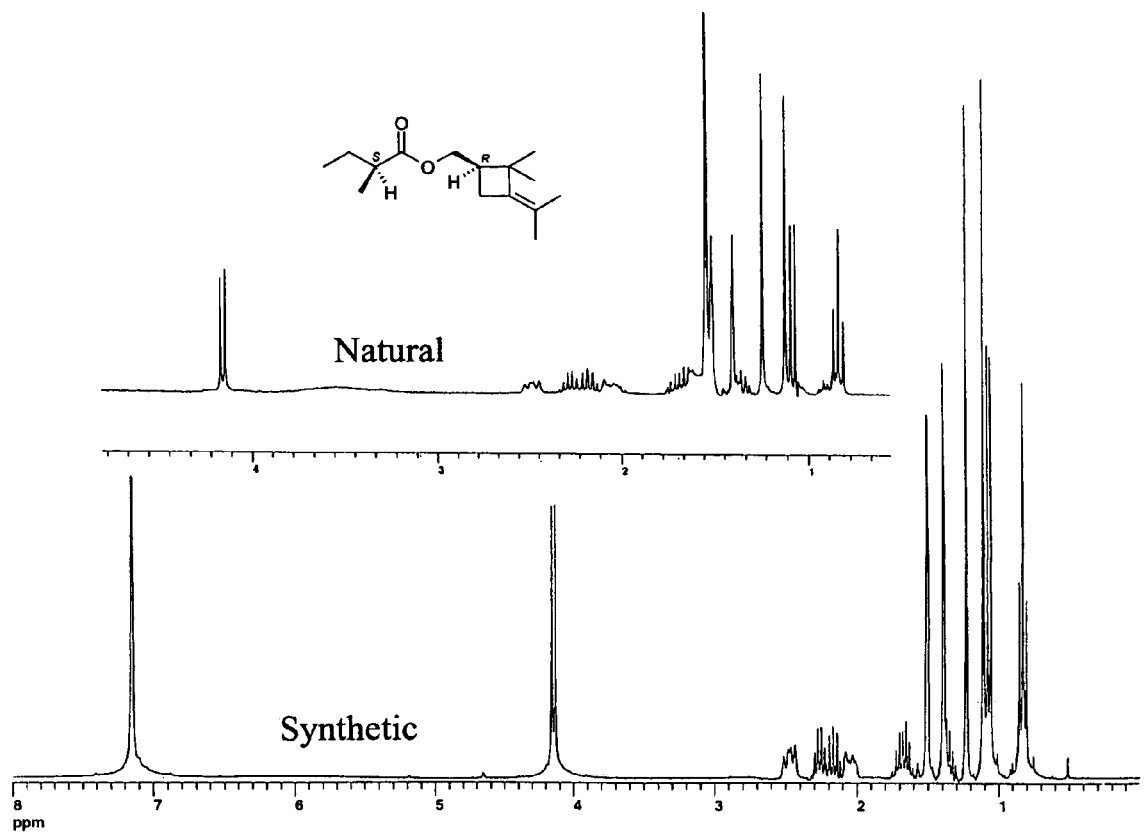
FIG. 4 shows $^1$H NMR spectra (300 MHz) and structure of (R)-maconelliyl (S)-2-methylbutanoate.

The absolute configuration of the natural pheromone was unambiguously determined by comparison of retention times of natural 2-methylbutyric acid, lavandulol, and maconelliol with synthetic stereoisomers on a chiral β-DEX 120 GC capillary column (Table 1). Accordingly, the absolute configurations were determined to be RS for both compounds 1 and 2. Furthermore, the $^1$H-NMR spectrum of synthetic maconelliyl 2-methylbutanoate was indistinguishable from that of the natural compound isolated from PHM (FIG. 4).

Discussion: *Maconellicoccus hirsutus* pheromone component, maconelliyl 2-methylbutyrate 2, contained a methylethylidene group on the ring, thus creating a novel type of cyclobutane derivative that has not been previously reported.

In summary, we discovered, identified, and synthesized two new compounds that together constitute the female sex pheromone of pink hibiscus mealybug, *M. hirsutus*: (R)-lavandulyl (S)-2-methylbutanoate) 1 and (R)-maconelliyl (S)-2-methylbutanoate 2. The specific ester with (R)-lavandulyl and (S)-2-methylbutanoic acid has not previously been described. Maconelliol is a novel cyclobutanoid monoterpene, and its structure has been established by enantioselective synthesis from precursors of known structure and configuration. A synthetic 1:5 mixture of the two RS pheromone components (1 and 10 μg/rubber septum) was an extremely potent attractant (as shown below). The synthetic mixture will be a useful tool for monitoring PHM flight activity and tracking biocontrol efforts. The identification of the sex pheromone will also enable future development of mating disruption and attract-and-kill technologies for managing *M. hirsutus* populations.

Enantioselective Synthesis of the Female Sex Pheromone of the Pink Hibiscus Mealybug, *Maconellicoccus hirsutus*:

General: NMR-spectra were recorded in $C_6D_6$ or $CDCl_3$ solution on a Bruker QE Plus spectrometer at 300 MHz for $^1H$, and 75 MHz for $^{13}C$, respectively. The chemical shifts were expressed in ppm (δ scale) relative to the residual solvent for $^1H(C_6H_6$ at δ 7.20 and $CHCl_3$ at 7.25 ppm), or to the central peak of solvent $^{13}C$ signal ($C_6D_6$ at 128.5 and $CDCl_3$ at 77.0 ppm). Low resolution electron impact (EI) gas chromatography-mass spectrometry (GC-MS) was conducted on a Hewlett-Packard (HP) 6890 GC coupled to a HP 5973 Mass Selective Detector using a 60 m×0.25-mm ID, 0.25-μm film-thickness DB-WAXETR capillary column (J&W Scientific Inc., Folsom, Calif.) with helium as carrier gas (50° C. for 2 min, then programmed to 230° C. at 15° C./min and held for 15 min). High resolution EI-MS (HREIMS) was measured on a Shimadzu GC-17A GC coupled to a JEOL JMS-SX102A mass spectrometer using a 15 m×0.25-mm ID, 0.25-μm film-thickness OV-5 capillary column (Ohio Valley Specialty Chemical, Marietta, Ohio) with helium as carrier gas (50° C., then programmed to 200° C. at 15° C./min and held for 15 min). A 70 eV electron beam was employed for sample ionization. Enantiomeric excess (ee) data were obtained on a HP 6890 GC equipped with a 30 m×0.25-mm ID, 0.25-μm film-thickness β-DEX 120 capillary column (Supelco, Inc., Bellefonte, Pa.) in the split mode (100:1) with hydrogen as carrier gas (55 cm/sec, 90° or 100° C. isothermal). Optical rotation was measured on a Perkin Elmer 241 Polarimeter at 24° C. Melting points were determined on a hot stage and were uncorrected. All reactions were performed under a nitrogen atmosphere with magnetic stirring unless otherwise indicated. All chemicals were obtained from Aldrich Chemical Co. and solvents were obtained from EM Science. Flash column chromatography was carried out on silica gel 60 (EM Science, 230-400 mesh) and solvents were evaporated using a Büchi RE 111 rotary evaporator.

(1R,3S)-(−)-3-(1-Hydroxy-1-methylethyl)-2,2-dimethylcyclobutanecarboxylic acid (3a). To a solution of 11.0 g (0.065 mol) of pinononic acid in 200 mL THF was added dropwise 65 mL (0.195 mol) of methyl magnesium chloride (3.0 M in THF). The reaction mixture was refluxed for 2 h on an 80° C. oil bath, then cooled, and treated with 50 g of ice water and 25 mL of concentrated HCl. The aqueous layer was separated and extracted with ether. The combined organic solutions were extracted with 1N $Na_2CO_3$. After washing with ether, the $Na_2CO_3$ solution was acidified with concentrated HCl and extracted again with ether. The combined extracts were washed with brine, dried over MgSO4, and concentrated to give 10.5 g white semi-solid. Recrystallization of the crude product (1:8=ethyl acetate:hexanes) gave 8.37 g (44 mmol) pure 3a in 67% yield. Optical purity: 80% ee; mp: 98-99° C.; $[α]^{24}_D$−5.0 (c 0.1, MeOH); $^1H$ NMR ($CDCl_3$): δ 1.10 (3H, s), 1.17 (3H, s), 1.22 (3H, s), 1.28 (3H, s), 1.8-2.0 (4H, bm), 2.1-2.4 (2H, m); $^{13}C$ NMR ($CDCl_3$): δ 176.26, 71.68, 51.88, 45.76, 44.39, 31.75, 29.06, 27.50, 19.71, 18.10; EI-MS m/z (%): 168 [M—$H_2O$] (3), 153 (21,) 128 (22), 123 (21), 110 (12), 101 (37), 99 (67), 83 (44), 71 (45), 69 (52), 59 (100), 56 (45), 43 (40). Conversion of pinononic acid to hydroxyacid 3 without epimerization at both stereogenic centers was essential. We tried different conditions with purified (1R,3S) pinononic acid by crystallization (>96% ee) as precursor. Reaction of methylmagnesium chloride with (1R,3S) pinononic acid formed an insoluble in THF intermediate bromomagnesium salt, the further reaction of which at the carbonyl group required either heating or sonication at r.t. As a result, partial epimerizations occurred at both centers. Methyllithium, on the other hand, gave with (1R,3S) pinononic acid a THF-soluble carboxylate that reacted with an additional 1.2 eq. of MeLi at −20° C., but still ~15% double epimerization took place. A solution was found by reacting (1R,3S) pinononic acid with 1.0 eq. MeLi at −20° C., followed by the addition of 1.6 eq. of MeMgCl, from which (1R,3S) 3a was isolated in 89% yield and 96% ee with virtually no change of chirality. This methodology can be used to scale up maconelliol (6) synthesis.

(1R,5S)-(+)-4,4,6,6-Tetramethyl-3-oxabicyclo[3.1.1]heptan-2-one (4a). To a solution of 2.66 g (14.28 mmol) of alcohol 3a in 15 mL of pyridine was added dropwise in 1.40 mL (15.00 mmol) of phosphorus oxychloride at ice-water cooling. The mixture was stirred at room temperature for 24 h, poured onto 75 g of ice, and extracted with ether. The ether extracts were washed with water, 2N hydrochloric acid, then water, saturated aqueous solution of sodium hydrogen carbonate, and brine. After drying over sodium sulfate, the solvent was removed, and the residue was purified by chromatography (30/70, ethyl acetate/hexanes) to afford 1.8 g (10.71 mmol) of pure lactone 4a in 75% yield. Optical purity: 80% ee; $[α]^{24}_D$+5.0 (c 0.1, MeOH); $^1H$ NMR ($CDCl_3$): δ 1.14 (3H, s), 1.37 (3H, s), 1.38 (3H, s), 1.49 (3H, s), 1.81 (1H, d, J=10.59 Hz), 2.10 (1H, dd, J=6.05, 5.67 Hz), 2.48 (1H, ddd, J=10.59, 5.67, 5.30 Hz), 2.63 (1H, dd, J=6.05, 5.30 Hz); $^{13}C$ NMR ($CDCl_3$): δ 175.04, 82.44, 50.34, 50.01, 40.91, 29.11, 26.11, 25.81, 25.27, 25.25; EI-MS m/z (%): 153 (26), 125 (20), 110 (40), 109 (55), 95 (100), 83 (27), 69 (72), 68 (78), 67 (60), 55 (42), 43 (35), 41 (38); HREIMS: obsd. 153.0911, calcd. for $C_9H_{13}O_2$ ($M^+$—$CH_3$): 153.0916.

(R)-(−)-2,2-Dimethyl-3-(1-methylethylidene)cyclobutanecarboxylic acid (5a). A solution of 3.68 g (21.9 mmol) of 4a in 60 mL of benzene with 416 mg (2.19 mmol) of p-toluenesulfonic acid monohydrate was heated in an oil bath at 100-110° C. for 24 h. A mini Dean-Stark trap was used for azeotropic distillation. Benzene was evaporated on a rotary evaporator, and the residue was treated with 2N aqueous $Na_2CO_3$ solution. The basic aqueous solution was washed with ether, then acidified to pH 2 with hydrochloric acid, and again extracted with ether. The combined ether extracts were washed with water, brine, dried, and concentrated to give 2.87 g (17.1 mmol, 78% yield) of 5a as clear oil after chromatography (silica gel, eluted with 20% to 25% of ethyl acetate in hexanes). Optical purity: 79% ee (after methylation); $[α]^{24}_D$−22.0 (c 0.1, MeOH); $^1H$ NMR ($CDCl_3$): δ 1.19 (3H, s), 1.37 (3H, s), 1.48 (3H, s), 1.58 (3H, s), 2.55 (1H, m), 2.81 (2H, m); $^{13}C$ NMR ($C_6D_6$): δ 183.49, 135.57, 123.27, 47.47, 45.09, 28.15, 25.94, 22.09, 19.51, 18.52; EI-MS m/z (%): 168 $[M]^+$ (38), 153 (38), 135 (8), 125 (21), 123 (27), 107 (59), 93 (29), 81 (100), 67 (30), 53 (16), 41 (25); HREIMS: obsd. 168.1152, calcd. for $C_{10}H_{16}O_2$ ($M^+$): 168.1150.

[(R)-(−)-2,2-Dimethyl-3-(1-methylethylidene)cyclobutyl]methanol [(R)-(−)-maconelliol] (6a). A solution of 2.1 g (12.5 mmol) of 5a in 30 mL of dry ether was stirred under a nitrogen atmosphere and cooled with an ice bath, while 713 mg (18.8 mmol) of lithium aluminum hydride was added in portions. The mixture was then stirred at room temperature overnight. To decompose excess hydride, 0.8 mL of water was added dropwise at ice bath temperature and stirred 15 min, followed by the addition of 0.8 mL of 10% aqueous sodium hydroxide solution and stirred another 15 min. After removing the ice bath, 2.4 mL of water was added and stirred for additional 30 min, then the solid was filtered off and washed with ether. The combined ether solutions were dried over $Na_2SO_4$, and concentrated to afford 2.0 g of clear oil.

Pure compound 6a (1.7 g, 11 mmol, 88% yield) was obtained by chromatography (silica gel, eluted with 15% to 20% of ethyl acetate in hexanes). Optical purity: 78% ee; $[\alpha]^{24}_D$−31.0 (c 0.1, MeOH); $^1$H NMR (CDCl$_3$): δ 1.15 (3H, s), 1.25 (3H, s), 1.38 (1H, br), 1.44 (3H, bs), 1.56 (3H, bs), 2.08 (2H, m), 2.58 (1H, bm), 3.62 (1H, dd, J=17.0, 11.4 Hz), 3.75 (1H, dd, J=17.0, 11.3 Hz); $^{13}$C NMR (CDCl$_3$): δ 179.85, 135.57, 123.27, 47.48, 45.09, 28.14, 25.93, 22.09, 19.51, 18.52; EI-MS m/z (%): 154 (17), 139 (18), 136 (13), 121 (59), 111 (14), 105 (12), 95 (34), 93 (28), 91 (15), 81 (100), 67 (23), 55 (14), 41 (20); HREIMS: obsd. 154.1362, calcd. for C$_{10}$H$_{18}$O (M$^+$): 154.1358.

(S)-(+)-Maconelliol (6b). Optical purity: 70% ee; $[\alpha]^{24}_D$+22.0 (c 0.1, MeOH).

[(R)-2,2-Dimethyl-3-(1-methylethylidene)cyclobutyl] methyl (S)-2-methylbutanoate [(R)-maconelliyl (S)-2-methylbutanoate] (2a). To a solution of 2.2 mL (20.1 mmol) of (S)-(+)-2-methylbutanoic acid {Aldrich, 99% ee, $[\alpha]^{24}_D$+24.0 (c 0.1, MeOH)} in 15 mL of benzene was treated with 2.2 mL (25.2 mmol) of oxalyl chloride and 10 μl of DMF. After 1.5 h at room temperature, the benzene and excess oxalyl chloride were removed followed by the addition of another 15 mL portion of benzene. The acid chloride residue was dissolved in 15 mL of benzene, and then a solution of 1.65 g (10.7 mmol) of 6a and 18 ml (22.2 mmol) of pyridine in 15 mL of benzene were added dropwise. After stirring at room temperature for 1 h, the solvent was removed. The residue was treated with 20 mL of water, and extracted with ether. The organic solution was washed with water, 1N hydrochloric acid, 1N aqueous sodium bicarbonate, and brine, dried over sodium sulfate, and concentrated to afford yellow oil. Pure 2a (2.0 g, 79% yield) was obtained by chromatography (silica gel, 2% of ethyl acetate in hexanes). Optical purity: 99% ee; $[\alpha]^{24}_D$−0.79 (c 2.03, MeOH); $^1$H NMR (C$_6$D$_6$): δ 0.84 (3H, t, J=7.19 Hz), 1.08 (3H, d, J=6.82 Hz), 1.12 (3H, s), 1.24 (3H, s), 1.36 (1H, m), 1.40 (3H, bs), 1.51 (3H, t, J=1.89 Hz), 1.67 (2H, m), 2.05 (1H, m), 2.17 (1H, m), 2.27 (1H, m), 2.48 (1H, ddt, J=14.75, 8.79, 1.52 Hz), 4.15 (2H, d, J=7.57 Hz); $^{13}$C NMR (C$_6$D$_6$): δ 175.76, 137.48, 122.55, 65.30, 44.43, 41.39, 39.71, 28.62, 27.79, 27.13, 21.17, 19.60, 18.64, 16.85, 11.80; EI-MS m/z (%): 238 [M]$^+$ (2), 136 (29), 121 (100), 107 (12), 93 (20), 81 (26), 67 (5), 57 (16), 41 (10); HREIMS: obsd. 238.1929, calcd. for C$_{15}$H$_{26}$O$_2$ (M$^+$): 238.1933.

[(R)-2,2-Dimethyl-3-(1-methylethylidene)cyclobutyl] methyl (R)-2-methylbutanoate [(R)-maconelliyl (R)-2-methylbutanoate] (2b). (R)-(−)-2-Methylbutyric acid (Shirali, S., and A. Zhang, Synth. Commun., 34: 3435-3441 (2004)) {99% ee, $[\alpha]^{24}_D$−24.0 (c 0.1, MeOH)}. Optical purity: 99% ee; $[\alpha]^{24}_D$−24.0 (c 0.1, MeOH); $^1$H NMR (C$_6$D$_6$): δ 0.84 (3H, t, J=7.51 Hz), 1.08 (3H, d, J=7.01 Hz), 1.12 (3H, s), 1.23 (3H, s), 1.33 (1H, m), 1.40 (3H, bs), 1.51 (3H, t, J=2.00 Hz), 1.67 (2H, m), 2.05 (1H, m), 2.17 (1H, m), 2.26 (1H, m), 2.48 (1H, ddt, J=14.77, 9.01, 1.50 Hz), 4.15 (2H, m); $^{13}$C NMR (C$_6$D$_6$): δ 175.74, 137.47, 122.55, 65.28, 44.41, 41.38, 39.75, 28.61, 27.80, 27.09, 27.18, 19.60, 18.63, 16.88, 11.80; MS (EI): m/z 238 [M]$^+$ (2), 136 (27), 121 (100), 107 (11), 93 (19), 81 (27), 67 (5), 57 (19), 41 (12).

[(S)-2,2-Dimethyl-3-(1-methylethylidene)cyclobutyl]methyl (S)-2-methylbutanoate [(S)-maconelliyl (S)-2-methylbutanoate] (2c). Optical purity: 97% ee; $[\alpha]^{24}_D$+16.0 (c 0.1, MeOH).

[(S)-2,2-Dimethyl-3-(1-methylethylidene)cyclobutyl]methyl (R)-2-methylbutanoate [(S)-maconelliyl (R)-2-methylbutanoate] (2d). Optical purity: 99% ee; $[\alpha]^{24}_D$−0.2 (c 2.03, MeOH).

(R)-2-Isopropenyl-5-methylhex-4-enyl (S)-2-methylbutanoate [(R)-lavandulyl (S)-2-methylbutanoate] (1a): Esterification of (R)-(−)-lavandulol {(86% ee, $[\alpha]^{24}_D$−9.6 (c 0.1, MeOH), prepared according to the method described by Cardillo et al. (Cardillo, G., et al., J. Org. Chem., 53: 2354-2356 (1988))} with (S)-(+)-2-methylbutanoic acid using the same procedures as compound 2a gave 75 mg (75% yield) of 1a as clear oil. Optical purity: 99% ee; $[\alpha]^{24}_D$+5.0 (c 0.1, MeOH); $^1$H NMR (C$_6$D$_6$): δ 0.83 (3H, t, J=7.29 Hz), 1.08 (3H, d, J=7.0 Hz), 1.35 (1H, m), 1.50 (3H, s), 1.59 (3H, t, J=0.80 Hz), 1.61 (3H, d, J=1.13 Hz), 1.68 (1H, m), 2.06 (2H, m), 2.28 (1H, sextet, 6.85 Hz), 2.42 (1H, quintet, 7.00 Hz), 4.12 (2H, m), 4.79 (1H, m), 4.83 (1H, quintet, J=1.51 Hz), 5.11 (1H, t, quintet, J=7.19, 1.52 Hz); $^{13}$C NMR (C$_6$D$_6$): δ 175.88, 146.31, 132.70, 122.00, 112.50, 66.68, 45.41, 41.22, 29.13, 26.00, 25.80, 20.00, 17.80, 16.50, 11.52; EI-MS m/z (%): 238 [M]$^+$ (1), 169 (2), 156 (3), 136 (15), 121 (39), 107 (11), 93 (100), 85 (23), 80 (25), 69 (75), 57 (59), 41 (40); HREIMS: obsd. 238.1934, calcd. for C$_{15}$H$_{16}$O$_2$ (M$^+$): 238.1933.

(R)-2-Isopropenyl-5-methylhex-4-enyl (R)-2-methylbutanoate [(R)-lavandulyl (R)-2-methylbutanoate] (1b). Optical purity: 99% ee; $[\alpha]^{24}_D$−11.0 (c 0.1, MeOH); $^1$H NMR (C$_6$D$_6$): δ 0.83 (3H, t, J=7.57 Hz), 1.08 (3H, d, J=7.19 Hz), 1.35 (1H, m), 1.50 (3H, s), 1.59 (3H, q, J=0.76 Hz), 1.61 (3H, d, J=1.10 Hz), 1.69 (1H, m), 2.07 (2H, m), 2.28 (1H, sextet, 6.81 Hz), 2.43 (1H, quintet, 7.00 Hz), 4.12 (2H, m), 4.79 (1H, m), 4.83 (1H, m), 5.12 (1H, t, quintet, J=7.00, 1.51 Hz); $^{13}$C NMR (C$_6$D$_6$): δ 175.74, 145.22, 132.62, 122.38, 112.69, 65.50, 46.84, 41.41, 28.99, 27.08, 25.79, 19.87, 17.78, 16.91, 11.79; MS (EI): m/z 238 [M]$^+$ (1), 169 (2), 156 (4), 136 (17), 121 (42), 107 (11), 93 (100), 85 (22), 80 (25), 69 (72), 57 (53), 41 (35).

(S)-2-Isopropenyl-5-methylhex-4-enyl (S)-2-methylbutanoate [(S)-lavandulyl (S)-2-methylbutanoate] (1c). {(S)-(+)-lavandulol, 81% ee, $[\alpha]^{24}_D$+10.0 (c 0.1, MeOH), prepared according to the method described by Cardillo et al. ((Cardillo, G., et al., J. Org. Chem., 53: 2354-2356 (1988))}. Optical purity: 98% ee; $[\alpha]^{24}_D$+10.0 (c 0.1, MeOH).

(S)-2-Isopropenyl-5-methylhex-4-enyl (R)-2-methylbutanoate [(S)-lavandulyl (R)-2-methylbutanoate] (1d). Optical purity: 99% ee; $[\alpha]^{24}_D$−8.0 (c 0.1, MeOH).

Results and discussion: Pinononic acid was a suitable intermediate for the preparation of novel 2 because it was easily obtained from α-pinene through the intermediate verbenone, and contained the required cyclobutane skeleton and useful functional groups. Allylic oxidation of (1R)-(+)-α-pinene (94% ee) at C$_4$ using molecular oxygen afforded (1R)-(+)-verbenone in moderate yield. Subsequently, oxidative cleavage of double bond in verbenone by using ruthenium trichloride/NaIO$_4$ (Moglioni, A. G., et al., J. Org. Chem., 65: 3934-3940 (2000)) resulted in target compound pinononic acid without epimerization.

Figure 6:
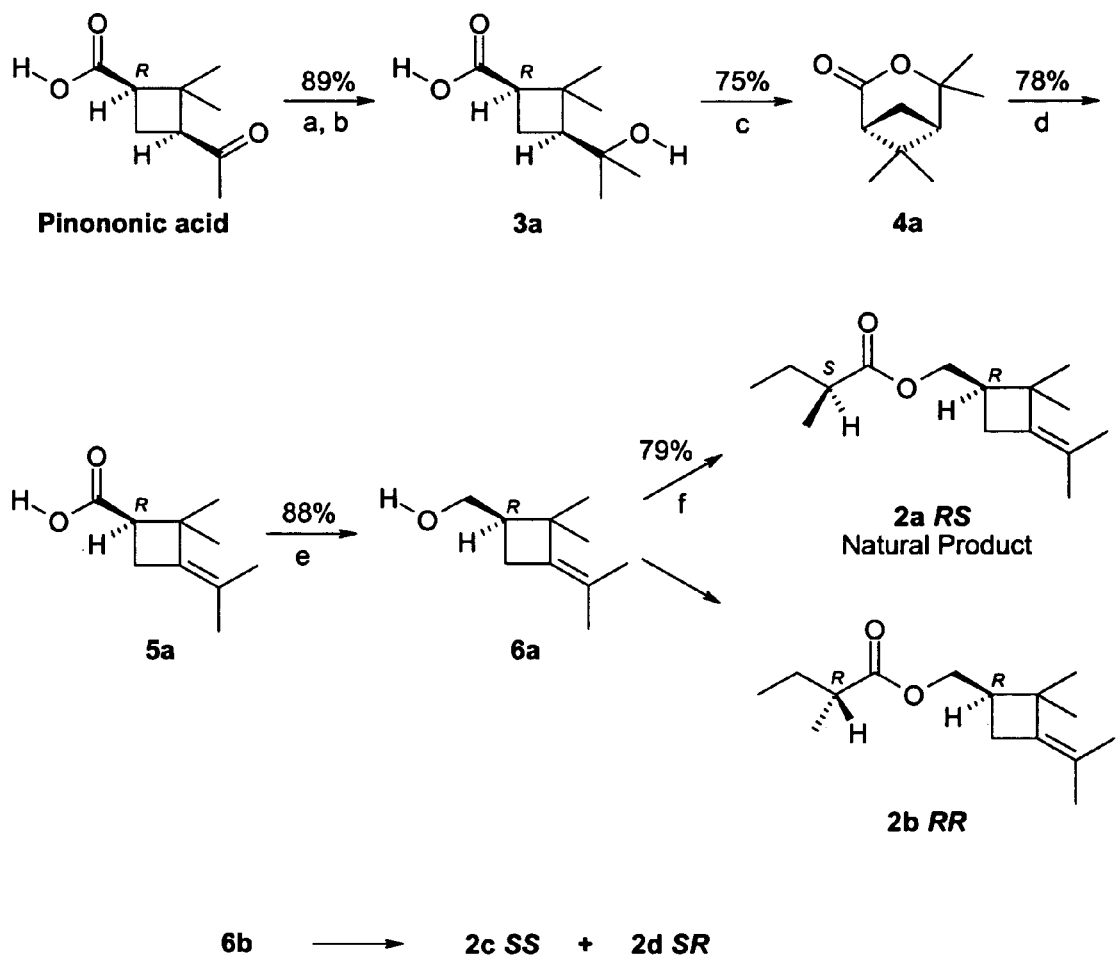
FIG. 6 shows enantioselective synthetic pathway of four different stereoisomers of maconelliyl-2-methylbutanoate: (a) MeLi/ether, 1.0 eq, THF, −20° C., 15 min; (b) MeMgCl/THF, 1.6 eq. −10° C., 30 min, rt, 1 h; (c) POCl$_3$/pyridine, rt, 24 h; (d) p-TsOH/C$_6$H$_6$, reflux, 24 h; (e) LiAlH$_4$/ether, rt, overnight; (f) EtCHMECOOH, ClCOCOCl/DMF/C$_6$H$_6$, rt, 1.5 h.

Pursuing the synthesis of structure 2, the required methylethylidene group was introduced by treating pinononic acid with a nucleophilic reagent to form the tertiary alcohol 3 and then introducing the double bond upon dehydration. Reaction of pinononic acid (94% ee) with three moles of Grignard reagent, CH$_3$MgCl, in THF resulted in the formation of a crude semi-solid, which could be recrystallized from ethyl acetate and hexanes to get pure 3a (80% ee). Partial loss of enantiomeric purity was due to double epimerization during nucleophilic addition. Conversion of pinononic acid to hydroxyacid 3 without epimerization at both stereogenic centers was achieved later in a small-scale reaction at different conditions. When the pinononic acid (>96% ee) reacted with 1.0 eq. MeLi at −20° C., a THF-soluble carboxylate solution was formed. Following an addition of 1.6 eq. of CH$_3$MgCl, 3a was isolated in 89% yield with virtually no change of chirality (96% ee) (FIG. 6).

With the geminal dimethyl tertiary alcohol 3a available, we then attempted dehydration of the alcohol to the desired methylethylidene product. To prevent decarboxylation during dehydration, 3a was first converted into its methyl ester using thionyl chloride in absolute methanol. We felt that the best chance of success for this transaction would involve use of a copper (II) triflate [Cu(OTf)$_2$] catalyst. Unfortunately, treatment of 3a with 0.1 mol-equivalent of Cu(OTf)$_2$ gave no useful result, even after extended periods of time at elevated temperatures.

Therefore, other dehydration catalysts were deployed. Approaches were made by treating the methyl ester of 3a with different reagents under following conditions: (a) 1.05 mole of POCl$_3$ in pyridine at room temperature for 24 h; (b) 1.1 mole of p-TsCl with equal amounts of DMAP in CH$_2$Cl$_2$ at room temperature for 6 h; and (c) 0.03 mole of p-TsOH in benzene at 100-110° C. refluxing for 24 h. In none of the cases could the desired compound be obtained exclusively. In experiment (a), a mixture of isopropenyl (56%) and methylethylidene compounds (44%) was obtained. In (b), no dehydration product was isolated. In (c), about 90% desired methylethylidene product was obtained but it still contained 10% of the isopropenyl isomer as a byproduct. The separation of these two isomers by column chromatography was difficult, owing to the similarity of chemical and physical properties. From the above experiments, it was concluded that it is impossible to prepare the required methylethylidene product solely by the above methods.

Successful dehydration was ultimately realized through a key intermediate 4. When the same experimental reagents and conditions were conducted with free acid 3, lactone 4 was obtained as a sole product in experiments (a) and (b). However, experiment (c) still gave the same mixture as reacting with methyl ester. Surprisingly, the lactone 4a was found to be easily converted to the desired methylethylidene compound 5 exclusively by the same reagent and conditions as described for experiment (c); refluxing lactone 4 in benzene with a catalytic amount of p-TsOH gave pure 5. Sole formation of the methylethylidene compound 5 without its isopropenyl isomer as a byproduct by above dehydration process could be confirmed by absence of geminal olefinic resonance in the $^1$H NMR spectrum from δ 4.4-6.6 ppm.

The identity of lactone 4a was established on the basis of observed $^3J_{H-H}$ values between axial methylene hydrogen H-7α (δ 1.81, $J_{7α,1}$=0 Hz, $J_{7α,5}$=0 Hz) and vicinal H-1, H-5 (δ 2.63, $J_{1,7α}$=0 Hz; δ 2.10, $J_{5,7α}$=0 Hz). Through this analysis, it was deduced that the dihedral angle between H-7α and two vicinal protons, H-1 and H-5, is about 90°, therefore, the coupling constants are zero and only a doublet resonance with $J_{gem}$ was observed ($J_{7α,7β}$=10.59 Hz). This coupling pattern was similar to that of bicyclic precursor, (1R)-(+)-verbenone, for which a doublet resonance of axial geminal hydrogen H-7α was observed at δ 2.06 ppm with $J_{gem}$=9.08 Hz (Bates, R. B., and V. P. Thalacker, J. Org. Chem., 33: 1730-1732 (1968)) (1.76 ppm in C$_6$D$_6$) (Uchio, Y., Tetrahedron, 34: 2893-2899 (1978)). A long range coupling with $^4J_{H-H}$=6.05 Hz between H-1 and H-5 was also observed because of the "W" configuration in the molecule 4a.

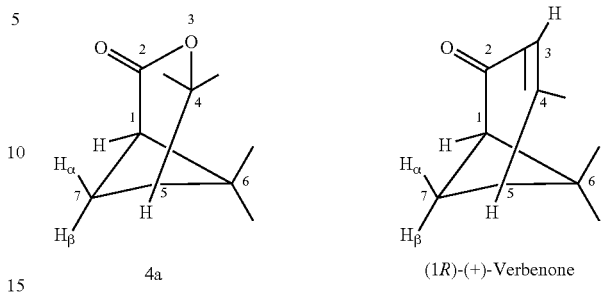

With methylethylidene compound 5 in hand the remaining steps were as follows: The resulting acid 5a was treated with LiAlH$_4$ in ether to furnish the (R)-(−)-maconelliol 6a {[α]$^{24}_D$−31.0 (c 0.1, MeOH)} in good yield, and its enantiomeric purity was determined to be 78% ee. Similarly, (1S)-(−)-verbenone (80% ee, commercially available) was also converted into (S)-(+)-maconelliol 6b {70% ee, [α]$^{24}_D$+22.0 (c 0.1, MeOH)}. The various spectral and GC data of synthetic (R)-(−)-6a were in good agreement with those of the natural product (Zhang, A., et al., Proc. Natl. Acad. Sci. U.S.A., 101: 9601-9606 (2004)). Thus, we were able to determine the absolute configuration of the naturally occurring maconelliol 6 to be R.

(S)-(+)-2-Methylbutyric acid was commercially available (>99% ee), and (R)-(−)-2-methylbutyric acids (Shirali, S., and A. Zhang, Synth. Commun., 34: 3435-3441 (2004)) was prepared in good yield, and with high ee (>99%) according to the method described by Cardillo et al. The both MS and chiral GC data of synthetic (S)-(−)-2-methylbutyric acid were in good agreement with those of the natural product (Zhang, A., et al., Proc. Natl. Acad. Sci. U.S.A., 101: 9601-9606 (2004)). Therefore, the absolute configuration of the naturally occurring acid was determined to be S.

Condensation of (S)-(+)- and (R)-(−)-2-methylbutyric acids with (R)-maconelliol 6a by using 1.25 mole of oxalyl chloride and catalytic amounts of DMF in benzene gave the esters 2a (RS) and 2b (RR) in good yields. Similarly, two other isomeric esters (SS and SR) were synthesized in this manner by using (S)-maconelliol 6b. Only one isomer, (R)-maconelliyl (S)-2-methylbutanoate 2a, was found to be indistinguishable from the natural product on the basis of both $^1$H NMR spectrum (Zhang, A., et al., Proc. Natl. Acad. Sci. U.S.A., 101: 9601-9606 (2004)), MS, and enantioselective chromatography criteria.

Figure 7:
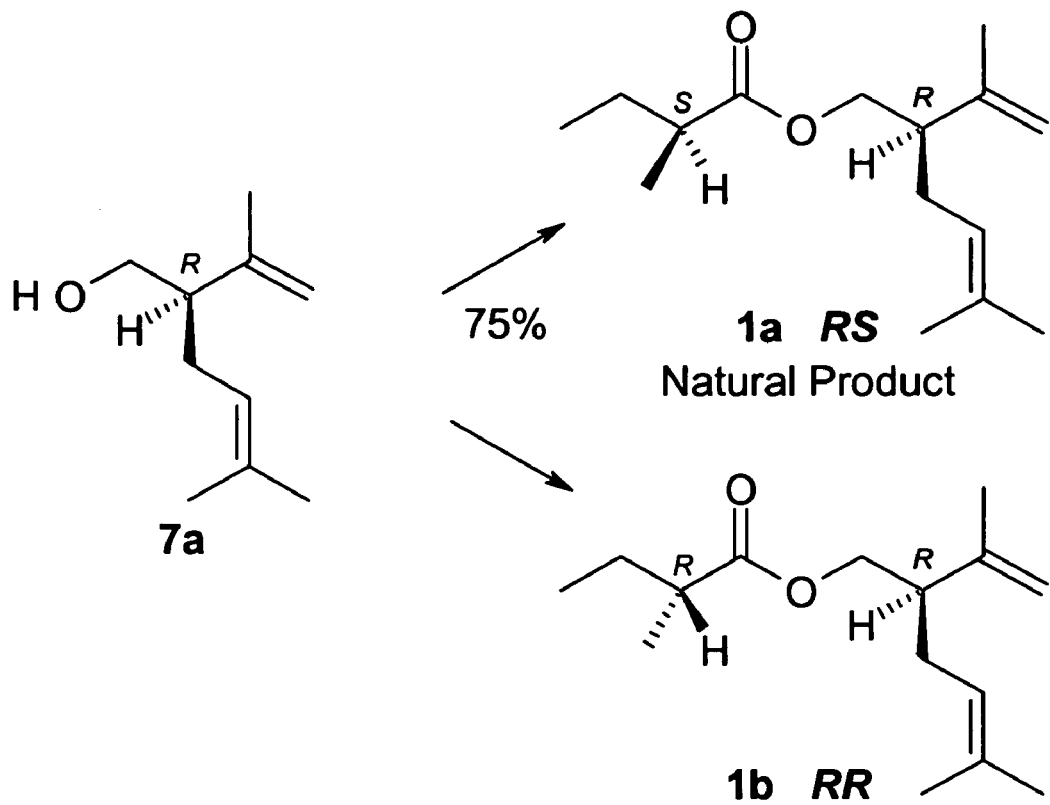
FIG. 7 shows synthetic pathway of four different stereoisomers of lavandulyl-2-methylbutanoate.

The minor pheromone component 1 was also prepared. (R)- and (S)-lavandulols 7 were enantioselectively synthesized according to the method described by Cardillo et al. After esterification (FIG. 7), only RS ester 1a was found to be indistinguishable from the natural product on the basis of $^1$H NMR spectrum, MS, and enantioselective chromatographic data. As a result, the sex pheromone of the pink hibiscus mealybug, M. hirsutus, was surprisingly identified to be a mixture of (R)-maconelliyl (S)-2-methylbutanoate and (R)-lavandulyl (S)-2-methylbutanoate. The absolute configuration of the pheromone components was established by comparison of the naturally occurring compounds with the optically active isomers derived from the enantioselective syntheses.

In conclusion, the 2,2-dimethyl-3-(1-methylethylidene) cyclobutane ("maconelliane") nucleus represents a heretofore undescribed natural product and has never been prepared synthetically.

Biological Activity Evaluation of the Sex Pheromone of the Female Pink Hibiscus Mealybug, *Maconellicoccus hirsutus* (Green) (*Homoptera*: Pseudococcidae):

Field bioassays: Gray halo-butyl rubber septa (5 mm, West Pharmaceutical Services, Kearney, Nebr.) were soxhlet extracted with acetone for 48 hr and dried in a fume hood before use. The cleaned septa were loaded with the desired rates of candidate pheromone components in ~40 μl of hexane solution, and used for field tests. The same amount of hexane was loaded on septa for the blank controls. The first experiment conducted in the field was to test the biological activity of all eight possible optical isomers of lavandulyl 2-methylbutanoate and maconelliyl 2-methylbutanoate at 1-μg dose in four binary combination (RS, SR, RR, and SS; within combination, components have the same configuration) at a molar ratio of 1:5 (lavandulyl 2-methylbutanoate:maconelliyl 2-methylbutanoate=1:5), which mimicked the blend ratio found in the female effluvia extracts. The following chemical treatments were loaded on rubber septa (ratios are molar ratios): 1-μg of the RS, SR, RR, and SS blends; 0.1, 1, 10, and 100-μg of the RS blend in the above ratio; 1 μg of the RS isomers of lavandulyl 2-methylbutanoate and maconelliyl 2-methylbutanoate in 1:0, 5:1, 1:1, 1:5, and 0:1 ratios; 1-μg of the RS blend, 1-μg of the RS blend +1-μg of the SR blend, 1-μg of the RR blend +1-μg of the SS blend (1:5 ratio); 1 and 10-μg of the RS blends +1 and 10-μg of the RS alcohol blends (1:5 ratio), respectively. After loading, the solvent was allowed to evaporate in a fume hood for 30 min. Lures were then wrapped in aluminum foil, stored in 20 ml plastic vials, and shipped by express carrier on the same day. Upon arrival, the lures were kept in a refrigerator at 4° C. until used in the field.

All of field bioassays were conducted in three locations in Key Biscayne, Fla. between July and January. White sticky cards (Pherocon V traps, Trécé, Salinas, Calif.) were used for the field bioassays. The infestation level in experimental sites ranged from moderate to severe. The lures were set in the trap cards by folding the trap inside out so that the grid and glue were visible on the outside. The die-cut perforations at the top of the trap were pushed out revealing two holes. The top hole was used to put the twist tie for hanging the traps and the lower hole for attaching the septum lure. The septum was inserted into the lower hole of the trap card and secured by pinning through the narrow end of the lure with an #2 insect pin. Each trap card was tied on a garden steel rod fastened to a branch. The cards on the rod were placed one foot above the hibiscus plants hedge top. Traps were arranged in a randomized complete block design with three replicates in each location and ca. 1 m intertrap distance within replicates. In each test, traps were replaced daily or weekly with the lure transferred to the new trap. Cards collected were put separately in transparent plastic bags and brought to the laboratory to count the trapped insects under a microscope. Lures were also collected and kept in a freezer at the end of each test.

Chemicals: (S)-(+)-2-Methylbutyric acid was commercially available (Aldrich, Milwaukee, Wis.). (R)-(−)-2-Methylbutyric acid, (R)-lavandulyl (S)-2-methylbutanoate, (R)-maconelliyl (S)-2-methylbutanoate, and other stereoisomers were obtained by enantioselective synthesis as discussed above. Purity of each isomer was found to be at least 92 percent and enantiomer excess (ee) was $\geq$97 percent (Table 2) as determined by a Hewlett Packard (HP) 6890 gas chromatography (GC) (Wilmington, Del.) with flame ionization detector using a 60 m×0.25-mm ID, 0.25-μm film-thickness DB-WAXETR capillary column (J&W Scientific Inc., Folsom, Calif.) in the splitless mode with hydrogen as carrier (80° C. for 2 min, then programmed to 250° C. at 15° C. per min and held for 15 min) or a 30 m×0.25-mm ID, 0.25-μm film-thickness β-DEX 120 capillary column (Supelco, Inc., Bellefonte, Pa.) in the split mode (100:1) with hydrogen as carrier (55 cm per sec, 100° C. isothermal). Optical rotation was obtained on a Perkin Elmer 241 Polarimeter (Perkin-Elmer Corp., Norwalk, Conn.) at 25° C.

Lure analysis: Three RS lures exposed in the field during the first wk and six RS lures collected at the end of the flight season were placed individually into 3 ml hexane in a 4-ml vial and soaked for 8 hr. Extracts (20 μl each) were diluted with hexane to an approximate volume (ca. 10 ng per μl) for gas chromatography-mass spectrometry (GC-MS) analyses. Electronic impact GC-MS analyses of pheromone lures were conducted on a Hewlett-Packard 6890 GC coupled to a HP 5973 Mass Selective Detector using a DB-WAXETR capillary column (J&W Scientific Inc., Folsom, Calif., 60 m×0.25-mm ID, 0.25-μm film-thickness, 50° C. for 2 min, then programmed to 230° C. at 15° C. per min and held for 15 min) with helium as carrier gas. A 70 eV electron beam was employed for sample ionization. The ions, m/z 93, 121, and 136 were selected as the monitor ions and remaining pheromone concentrations were obtained by comparison with synthetic RS pheromone standards at the same conditions.

Statistical analysis: Unless otherwise specified, the counts of insect captured were converted to proportion (p) of total captured insect within replicate because of considerable variations in the numbers of insect captured between replicates. The data were then transformed by the standard variance stabilizing transformation for proportions (arcsin $\sqrt{p}$) in order to fit the assumption of homogeneity of variances for analysis of variance (ANOVA). Means were compared by one-way ANOVA followed by Ryan-Einot-Gabriel-Welsch Range test (SPSS 10.0 for Windows, George and Mallery 2002) for significance at $\alpha$=0.05.

Figure 8:
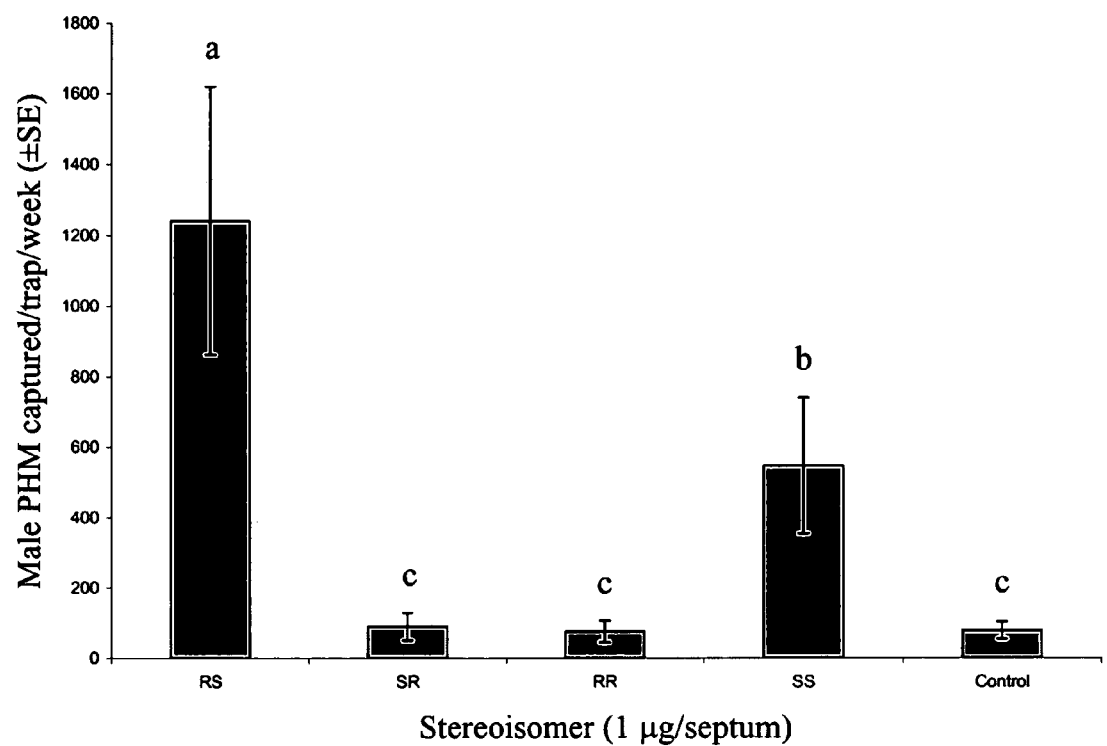
FIG. 8 shows number (mean±SEM) of male M. hirsutus caught in sticky traps baited with various binary isomeric blends and a blank. The test was conducted in July and traps lures were replaced weekly. The total number of male M. hirsutus captured was 18,291. Means followed by the different letters are significantly different at α=0.05 (N=9, F=62.87; df=4,10; P<0.001).

Results: In the three wk period in July, all traps baited with RS isomeric blend (natural configuration) were more attractive to males than the other blends (F=62.87; df=4,40; P<0.001), with mean trap catches over all treatments varying from 388 to 3,202 males per wk per trap, indicating that RS binary optical isomers (the stereoisomers produced by *M. hirsutus*) were far more effective at capturing males than are non-biological isomer blends (FIG. 8). All traps baited with SS isomeric blend captured fewer males, but still significantly more attractive than SR, RR isomeric blends and control, suggesting that male *M. hirsutus* were able to discriminate the different optical isomers.

In the course of this field test, parasitoid activity was also very high. A total of 1,342 of the parasitoids, *A. kamali* and *G. indica*, were caught in the baited and blank sticky traps. There was no significant difference in the number of parasitoid caught in pheromone-baited and control traps (F=0.321; df=4,40; P=0.862) (Table 3).

Figure 9:
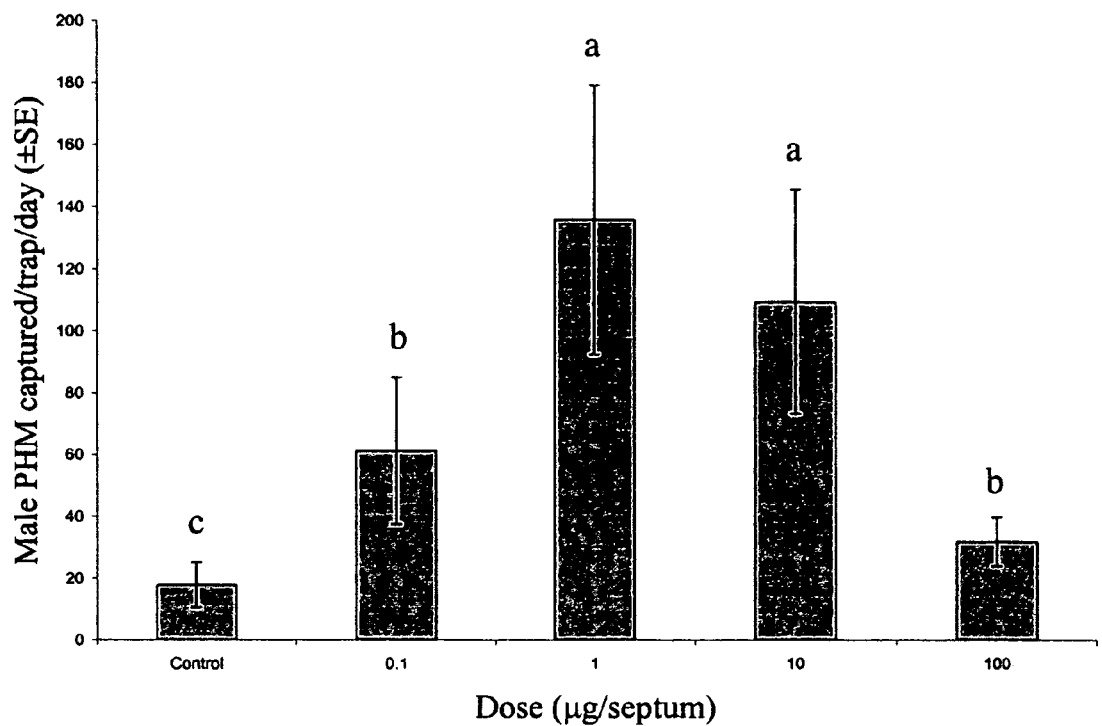
FIG. 9 shows results of M. hirsutus pheromone dose response field tests (RS binary isomers in 1:5 ratio). The assay was conducted from July to August and traps were replaced daily. The total number of male M. hirsutus captured was 5,095. Means followed by the different letters are significantly different at α=0.05 (N=12, F=24.59; df=4,55; P<0.001).

After determination that the RS binary blend was the most active blend, rubber septa containing RS pheromone in 1:5 ratio at 0.1 to 100-μg doses were evaluated to determine the optimized loading of pheromonal components. Male *M. hirsutus* catch was not significantly different in traps baited with 1 or 10-μg doses (FIG. 9). Traps baited with 0.1 and 100-μg doses captured significantly fewer mealybugs than did traps baited with 1 or 10-μg doses (F=24.59; df=4,55; P<0.001).

Figure 10:
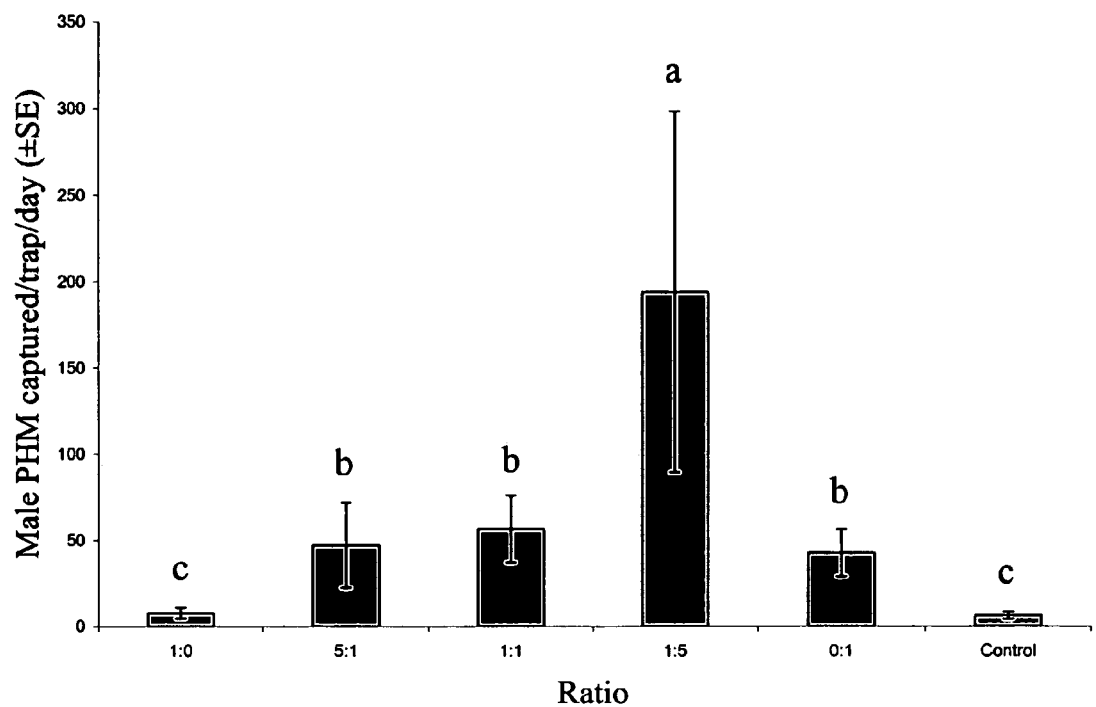
FIG. 10 shows captures of male M. hirsutus in traps baited with different ratio of two RS isomers and a blank control. The test was conducted from in August and traps were replaced daily. The total number of male M. hirsutus captured was 4,259. Means followed by the different letters are significantly different at α=0.05 (N=12, F=28.66; df=5,66; P<0.001).

With the 1-μg loading, the optimization of the ratios of two RS pheromone components for attraction was performed (FIG. 10). The results demonstrated that a ratio of (R)-lavandulyl (S)-2-methylbutanoate and (R)-maconelliyl (S)-2-methylbutanoate in 1:5 was significantly superior to the other ratios (F=28.66; df=5,66; P<0.001). This ratio was consistent with the natural ratio found in female effluvial collections.

Figure 11:
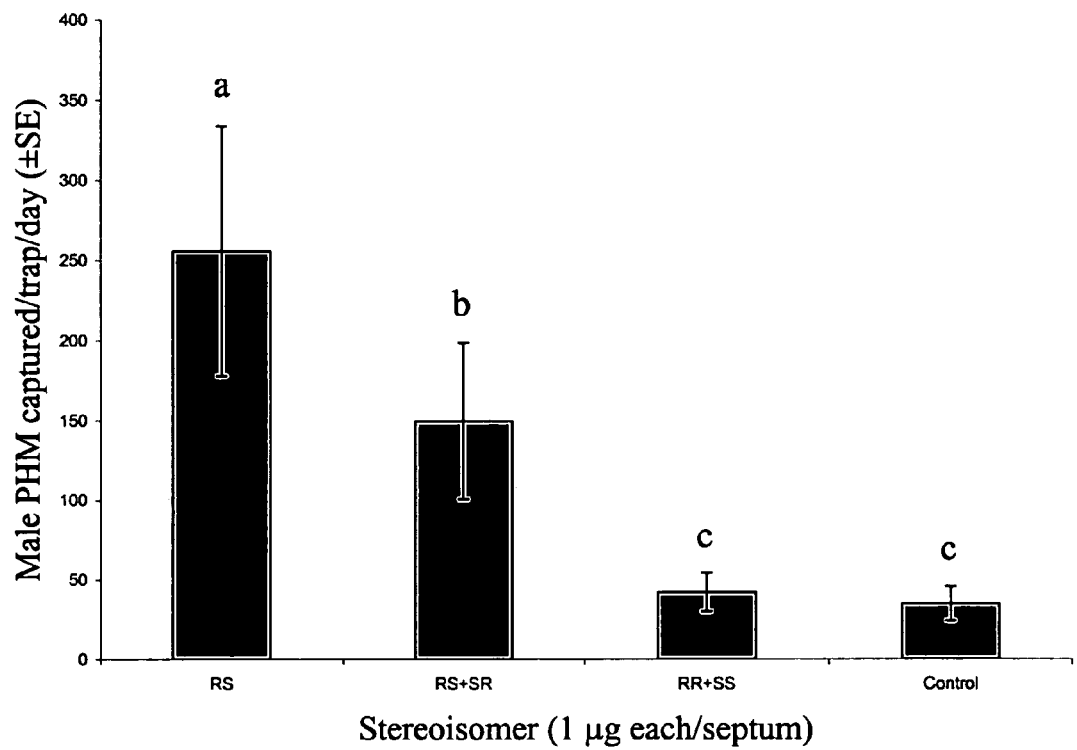
FIG. 11 shows effect of addition of the same amount and ratio of enantiomers to RS and SS isomers on captures of male M. hirsutus. The assay was conducted in August and traps were replaced daily. The total number of male M. hirsutus captured was 5,973. Means followed by the different letters are significantly different at α=0.05 (N=12, F=56.71; df=3, 44; P<0.001).

Inasmuch as the male *M. hirsutus* trap captures suggested chiral discrimination by the insect, the RS and SS isomers were evaluated at the natural ratio (1:5) with the same amount and ratio of their optical antipodes (FIG. 11). It was found that SR isomers significantly reduced attraction of RS pheromones, indicating that unnatural enantiomers antagonized attraction. Similarly, activity of SS isomers was decreased by adding the same amount of RR isomers ($F_{3,44}$=56.71; df=3, 44; P<0.001).

Figure 12:
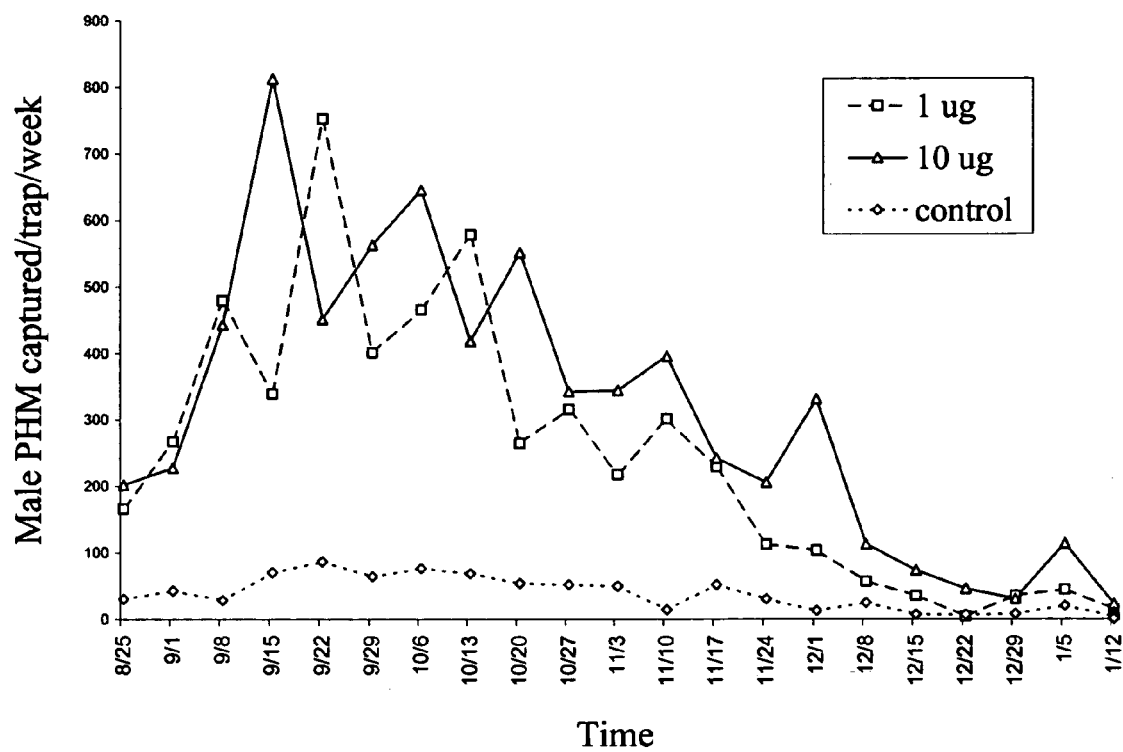
FIG. 12 shows mean numbers of male M. hirsutus caught in traps baited with 1 and 10 μg of RS isomers and blank control for a period of 21 wk from August to January. The total number of male M. hirsutus captured was 35,298 in pheromone-baited traps and 2,357 in control traps.

Lure release rate and longevity were evaluated using lures that had been loaded with 1 and 10-µg doses of RS isomers and exposed in the field. GC-MS analyses indicated that ~17 percent of the pheromone was evaporated, and ~0.83-µg pheromone remained in the rubber septa lures with 1-µg dose exposed for 1 wk in the field in July. With the same 1-µg dosage, about 82 percent of the pheromone evaporated, and ~0.18-µg pheromone still remained in the rubber septa exposed for 21 wk in the field from August to January. Correspondingly, ~86 percent of the pheromone evaporated from the rubber septa loaded with 10-µg dose, and ~1.39-µg pheromone remained after the same period (Table 4). During these 21 wk of field tests, more than 35,000 males were caught in RS pheromone-baited traps, whereas control traps caught less than 2,000 males. Although ~1.39 and ~0.18-µg pheromone still remained in the lures with 10 and 1-µg doses, the trap catches declined in December as winter approached and *M. hirsutus* populations declined (FIG. 12). In addition, the same efficacy of 1 or 10-µg doses was confirmed again in this test.

Figure 13:
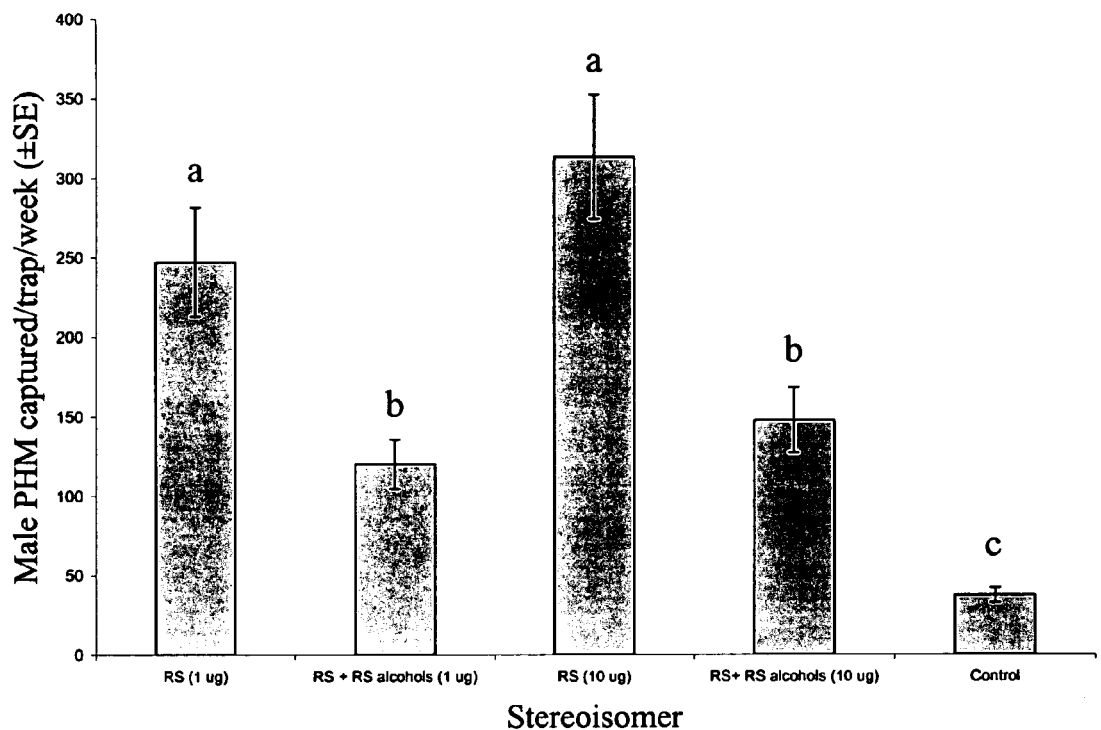
FIG. 13 shows effect of addition of (R)-lavandulol and (R)-maconelliol to RS isomers of pheromone esters on captures of male M. hirsutus. The assay was conducted from August to January and traps were replaced weekly. The total number of male M. hirsutus captured was 54,542. Means followed by the different letters are significantly different at α=0.05 [logarithm transformed (log x+1), N=63, F=17.00; df=4,310; P<0.001].

In the course of the same assay, (R)-lavandulol and (R)-maconelliol, which could be detected in the natural effluvial extracts, were also tested with the equal amount of ester (RS isomers) at 1 and 10-µg doses (FIG. 13). It was found that the alcohols significantly reduced attraction to the RS isomers (F=17.00; df=4,310; P<0.001).

Figure 14:
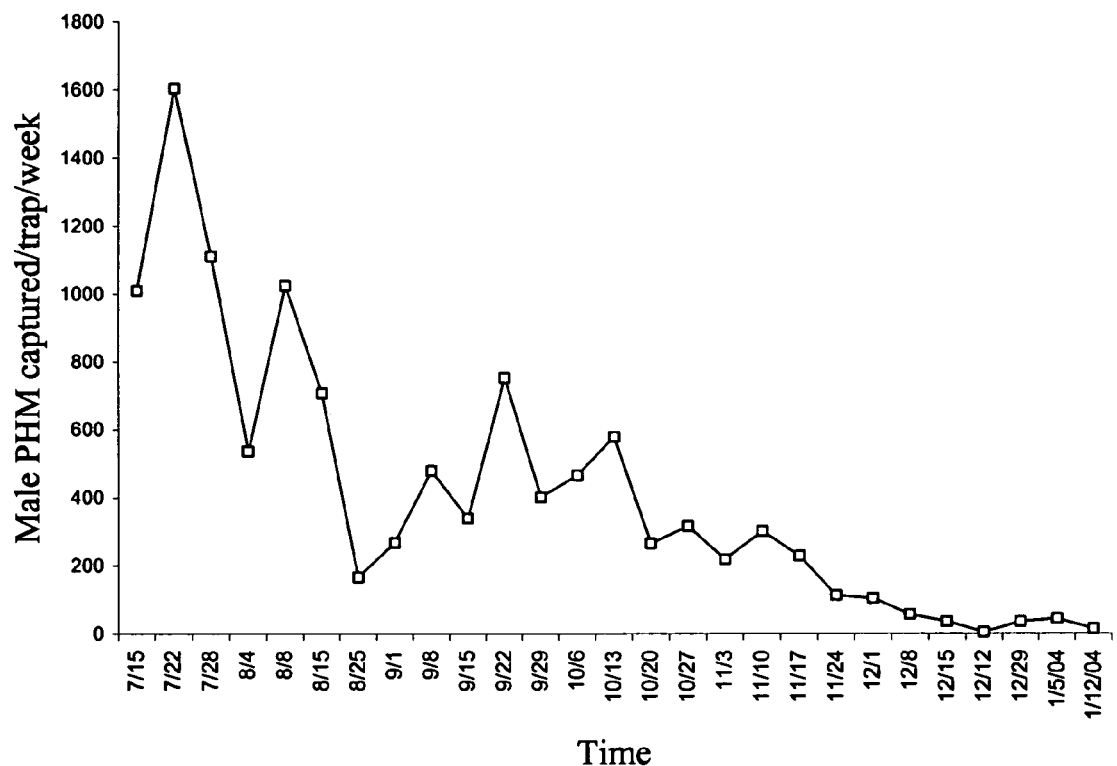
FIG. 14 shows the flight activity of M. hirsutus monitored using white sticky cards (Pherocon V traps, Trécé, Salinas, Calif.) baited with 1-μg RS isomers on gray rubber septa. The test was conducted from July to January. The total number of male M. hirsutus captured was 33,542.

The flight activity of *M. hirsutus* was monitored using 1-µg RS isomers-baited traps. The test was conducted from July to January and total number of male *M. hirsutus* captured was 33,542 (FIG. 14).

Discussion: The results of our field trapping studies with different binary optical isomeric blends versus blank control traps clearly indicate that RS isomeric blend at a ratio of 1:5 is surprisingly the most attractive blend to male *M. hirsutus* (FIG. 8). During this three wk period, a total of 18,291 *M. hirsutus* males were caught, with >61 percent of them being captured in traps baited with the RS blend. High biological activity of the RS blend not only confirms our pheromone identification (Zhang, A., et al., Proc. Natl. Acad. Sci. U.S.A., 101: 9601-9606 (2004)) but also demonstrates the enantiomeric specificity of male *M. hirsutus* pheromone perception. Interestingly, about 27 percent of male *M. hirsutus* were also lured into traps baited with the unnatural SS blend, whereas the other unnatural SR and RR blends each only caught ~4 percent of the males, which were equivalent to captures in the blank control. Without being bound by theory, the significant activity of the unnatural SS blend suggests that the chirality of the acidic moiety was more critical than that for the alcoholic moiety of the pheromone molecule.

Our dose-response test surprisingly demonstrated that 1 and 10 µg doses of RS isomers caught more males than lower and higher doses (FIG. 9). This finding indicated that male *M. hirsutus* were highly sensitive to pheromone concentration. Flight orientation toward a pheromone source was triggered and antagonized within a narrow range of pheromone concentration. For population monitoring purposes, low and high concentration thresholds need to be considered. On the other hand, males were confused or repelled by relatively high concentration of pheromone, suggesting that mating disruption may be a feasible management tool for this pest.

Our field test result surprisingly indicated that male *M. hirsutus* was sensitive to the presence of unnatural optical antipodes. Equal amount of unnatural SR enantiomeric blend antagonized natural RS blend attraction, so trap catches of the RS blend were dramatically reduced by about 42 percent (FIG. 11). A similar result was seen for the RR blend, although the SS blend has an unnatural configuration. This result revealed that male *M. hirsutus* can recognize both enantiomers. The natural RS blend yielded high trap captures, whereas the unnatural SR blend reduced captures. This was the first report of enantiomeric antagonism in the recognition behavior from mealybugs or scale insects.

In the course of the pheromone collection, significant amount of the alcoholic moieties, lavandulol and maconelliol, of the sex pheromone esters were also found in the volatile extracts. These two alcohols were not considered as the pheromone components because they did not elicited any antennal activity (Zhang et al. 2004). The result of field bioassay also clearly demonstrated that they were not required for the lure attractiveness. However, when the same amount and ratio of RS alcohols were mixed with 1 and 10 µg doses of RS isomeric pheromone blend, surprisingly attraction of male *M. hirsutus* was significantly reduced (FIG. 13).

The captures in RS isomers-baited traps were influenced by climatic factors during the flight season and other factors, such as parasitoids applications. However, trap captures with 1 µg of RS isomers indicated that there were many peaks, suggesting that there appears to be multiple generations during the tested period of July to January (FIG. 14).

The results from lure longevity and release rate studies indicate that pheromone lures should have an effective lifetime of about 21 wk (FIG. 12). This experiment was terminated in January, only because of the seasonal decline in *M. hirsutus* populations, rather than decline in the lure attractiveness. Chemical analyses of lures revealed that ~0.18 and ~1.39 µg of pheromone remained in the 1 and 10 µg dose septa, respectively, after 21 wk of field exposure (Table 4). These mounts of residual pheromones should still be sufficient to trigger and maintain the lure attraction for some time. Considering that release rate is affected by the temperature as well as wind speed, the dose of 1 µg is not recommended for a period over 6 months. The lure loaded with 10 µg dose of pheromone should maintain the attraction efficacy for at least 12 months.

In conclusion, the available evidence indicates that a binary blend containing two isomeric pheromone components, (R)-lavandulyl (S)-2-methylbutanoate and (R)-maconelliyl (S)-2-methylbutanoate, in a ratio of 1:5 on a rubber septum was highly attractive to males of *M. hirsutus* in the field. With the recent arrival of this invasive species on California and Florida, as well as in Mexico and Central America, timely detection of the *M. hirsutus* infestation is important to track the biological control efforts against this pest. The synthetic pheromone could provide an economical, convenient, and useful detection and monitoring tool, and eliminate the problems associated with the use of virgin females as the attractive source. Furthermore, the observation that relatively high concentration of pheromone suppress trap capture, suggests that mating disruption technique could be a potential tool for management of this pest. In addition, surprisingly parasitoids were not lured to synthetic pheromone source and relatively low numbers of natural enemies were caught in the sticky traps (Table 2), indicating that mass trapping for suppression of the *M. hirsutus* would not interfere with biological control eradication programs by APHIS currently underway in the Caribbean region.

All of the references cited herein are incorporated by reference in their entirety. Also incorporated by reference in their entirety are the following references: Akino, T., et al., Entomol. Science, 4: 271-277 (2001); Anonymous, The Hibiscus or Pink Mealybug, United States Department of Agriculture, Animal and Plant Health Inspection Service (1996), http://www.aphis.usda.gov/lpa/pubs/fsheet_faq_notice/fs_phphmealybug.html; Anonymous, Pink Hibiscus Mealybug *Maconellicoccus hirsutus* (Green), United States Department of Agriculture, Animal and Plant Health Inspection Service (2002), http://www.doacs.state.fl.us/pi/enpp/ento/pink.htm; Arai, T., et al., J. Chem. Ecol., 29: 2213-2223 (2003); Bates, R. B., and V. P. Thalacker, J. Org. Chem., 33: 1730-1732 (1968); Bierl-Leonhardt, B. A., et al., Tetrahedron Letters, 22: 389-392 (1981); Bierl-Leonhardt, B. A., et al., Life Sci., 27: 399-402 (1980); Bloor, S. J., Tetrahedron Letters, 34: 5617-5620 (1993); Bohlmann, F., et al., Chem. Ber., 106: 2904-2909 (1973); Bohlmann, F., et al., Phytochemistry 21, 2691-2697 (1982); Booth, D. C., et al., Journal of Chemical Ecology, 9: 1-12 (1983); Brenner, M., and M. Huber, Helv. Chim. Acta, 36: 1109-1115 (1953); Budavari, S., The Merck Index, (Merck & Co. Inc., Rahway), 11th Ed., pp. 287 (1989); Carde, R. T., and J. S. Elkinton, Field trapping with attractants: methods and interpretation, pp. 112-129, In H. E. Hummel and T. A. Miller [eds.], Techniques in Pheromone Research, Springer-Verlag, New York (1984); Carter-Lane, S., and J. Redding, Exotic Parasitic Wasps to Attack Invasive Mealybug in California, United States Department of Agriculture, Animal and Plant Health Inspection Service (1999), http://www.aphis.usda.gov/lpa/news/1999/09/MELBUGCA.HTM; Cardillo, G., et al., J. Org. Chem., 53: 2354-2356 (1988); Close, W. J., J. Org. Chem., 15: 1131-1134 (1950); Dunkelblum, E., Scale insects, pp. 251-276, In J. Hardie and A. K. Minks [eds.], Pheromones of non-lepidopteran insects associated with agricultural plants, CAB, Wallingford, UK (1999); Einhorn, J., et al., Acad. Sci. III, 296: 861-863 (1983); Einhorn, J., et al., Proc. Natl. Acad. Sci., 95: 9867-9872 (1998); Erickson, H. K., and C. D. Poulter, J. Am. Chem. Soc., 125: 6886-6888 (1993); Etienne, J., et al., Bulletin de la Societe entomologique de France, 103: 173-174 (1998)); Facundo, H. T., et al., Environ. Entomol. 23: 1508-1515 (1994); Fieser, L. F., and M. Fieser, Reagents for organic synthesis, Vol. 1; John Wiley & Sons, Inc.: New York, pages 1175-1176 (1967); Francke, W., et al., Pure and Applied Chemistry, 16: 539-542 (1989); Goolsby, J. A., et al., Florida Entomol. 85: 494-498 (2002); Hedin, P. A., et al., Journal of Chemical Ecology, 23: 965-977 (1997); Hinkley, S. F., et al., Tetrahedron Letters, 35: 3775-3776 (1994); Hoy, M. A., et al., http://edis.ifas.ufl.edu/BODY_IN156, University of Florida, 2002; Kairo, M. T. K., et al., International Pest Management Reviews, 5: 241-254 (2000); King, H. C. A., et al., J. Chem. Soc., 5449-5457 (1963); Ichihara, A., et al., Tetrahedron Lett., 28: 1175-1178 (1987); Laali, K., et al., Helv. Chim. Acta, 70: 607-611 (1987); Lajunen, M., and A. M. P. Koskinen, Tetrahedron Lett., 35: 4461-4464 (1994); Leal, W. S., Proc. Natl. Acad. Sci. U.S.A., 93: 12112-12115 (1996); Matile-Ferrero, D. and J. Eitienne, Revue Francaise d'Entomologie, 18: 38 (1996); Medley, T. L., Field releases of nonindigenous species of Anagyrus and Gyranusoidae for biological control of pink hibiscus mealybug, *Maconellicoccus hirsutus*, Environmental Assessment, Fed. Reg. 62, 34043, USDA-APHIS, Washington, D.C. (1997); Michaud, J. P., and G. A. Evans, Florida Entomol. 83: 97-101 (2000); Millar, J. G., et al., J. Econ. Entomol. 95: 706-714 (2002); Moffett, R. B., Org. Synth. Coll., IV, 834-835 (1963); Nakahata, T., et al., Biosci. Biotechnol. Biochem., 67: 2627-2631 (2003); Nie, J., et al., Med. Chem. Res., 318-331 (1996); Norte, M., et al., Tetrahedron Letters, 35: 4607-4610 (1994); Oliver, J. E., et al., Tetrahedron, 56: 7633-7641 (2000); Phillips, T. W., et al., Journal of Chemical Ecology, 10: 1417-1423 (1984); Polavarapu, S., and W. D. Seabrook, Can. Entomol. 124: 815-825 (1992); Screttas, C. G., and I. C. Smonou, J. Org. Chem., 53: 893-894 (1988); Serrano, M., et al., Environ. Entomol., 30: 339-345 (2001); Seals, L., The Pink Hibiscus Mealybug, The Sapodilla Times, 5: 2 (2002); Stibick, J. N. L., New pest response guidelines: Pink hibiscus mealybug *Maconellicoccus hirsutus*, United States Department of Agriculture, Animal and Plant Health Inspection Service (1997); Tomas, A. F., et al., Helv. Chim. Acta, 56: 238-239 (1973); Tumlinson, J. H., et al., Science, 166: 1010-1012 (1969); Uchio, Y., Tetrahedron, 34: 2893-2899 (1978); Utermoehlen, C. M., et al., J. Org. Chem., 52: 5574-5582 (1987); USDA-APHIS Pest alert: The pink hibiscus mealybug, http://aphisweb.aphis.usda.gov/oa/pubs/phmpaler.pdf, APHIS 81-35-005, 1999; Weyerstahl, P., et al., Fragrance J., 14: 112-120 (1999); Weyerstahl, P., et al., J. Essent. Oil Res. 4: 319-324 (1992); Williams, D. J., Bull. Entomol. Res., 86: 617-628 (1996); Zhang, A., et al., J. Chem. Ecol. 20: 2415-2427 (1994); Zhang, A., et al., J. Chem. Ecol., 23: 231-245 (1997); Zhang, A., et al., J. Chem. Ecol., 25: 1221-1232 (1999); Zhang, A., and S. Polavarapu, J. Chem. Ecol., 29: 2153-2164 (2003); Zhang, A., and S. Polavarapu, J. Chem. Ecol., 30: 1513-1527 (2004); Zhang, A., et al., Tetrahedron Letters, 45: 9401-9403 (2004); Zhang, A., et al, PNAS, 101: 9601-9606 (2004).

Also incorporated by reference in their entirety are the following U.S. Pat. Nos. 6,177,073; 5,505,951; 5,296,220; 5,167,955.

Thus, in view of the above, the present invention concerns (in part) the following:

A (synthetic or isolated) cyclobutane having the formula:

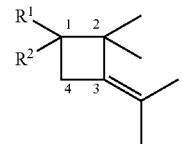

wherein $R^1$ is hydrogen, a $C_{1-11}$ straight or branched alcohol, aldehyde, alkyl, ether (e.g. methanol, ethanal, 4-methylhexane, heptyloxymethane), or esters thereof with a $C_{1-10}$ saturated or unsaturated, straight or branched acid (e.g., formic acid, acetic acid, 2-methylbutyric acid, 3-methyl-2-butenoic acid) and $R^2$ is hydrogen, methyl, $C_{2-10}$ saturated or unsaturated, straight or branched alkyl (e.g. hexane, isopropenyl, 4-methyl-4-pentene).

The above cyclobutane, wherein said acid is formic acid, acetic acid or 2-methylbutyric acid.

The above cyclobutane, wherein $R^1$ is methyl pantanoate and $R^2$ is hydrogen.

The above cyclobutane, wherein $R^1$ is methyl 2-methylbutanoate and $R^2$ is hydrogen. The above cyclobutane, wherein said cyclobutane is (R)-maconelliyl (S)-2-methylbutanoate.

The above cyclobutane, further comprising a carrier material or carrier (e.g., an agronomically acceptable carrier).

The above cyclobutane, further comprising (R)-lavandulyl (S)-2-methylbutanoate.

A composition comprising (or consisting essentially of or consisting of) at least one cyclobutane having the formula:

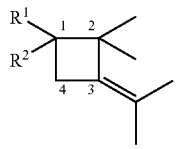

wherein $R^1$ is hydrogen, a $C_{1-11}$ straight or branched alcohol, aldehyde, alkyl, ether, or esters thereof with a $C_{1-10}$ saturated or unsaturated, straight or branched acid and $R^2$ is hydrogen, methyl, or $C_{2-10}$ saturated or unsaturated, straight or branched alkyl; optionally (R)-lavandulyl (S)-2-methylbutanoate, and optionally a carrier material or carrier (e.g., an agronomically acceptable carrier); preferably one of the cyclobutanes is (R)-maconelliyl (S)-2-methylbutanoate. Wherein the composition acts as an attractant for male pink hibiscus mealybugs. Wherein the composition acts as a mating disrupter for male pink hibiscus mealybugs.

The above composition, wherein one of said cyclobutanes is (R)-maconelliyl (S)-2-methylbutanoate.

The above composition, wherein said composition contains (R)-lavandulyl (S)-2-methylbutanoate.

The above composition, wherein the molar ratio of said (R)-lavandulyl (S)-2-methylbutanoate:(R)-maconelliyl (S)-2-methylbutanoate is about 1:about 2 to about 1:about 10 (preferably about 1:about 5).

The above composition, wherein said composition contains a carrier material or carrier (e.g., an agronomically acceptable carrier).

A (synthetic or isolated) composition for attracting male pink hibiscus mealybugs, comprising (or consisting essentially of or consisting of) a male pink hibiscus mealybug attracting effective amount of (R)-lavandulyl (S)-2-methylbutanoate and (R)-maconelliyl (S)-2-methylbutanoate, and optionally a carrier material or carrier (e.g., an agronomically acceptable carrier).

The above composition, wherein the molar ratio of said (R)-lavandulyl (S)-2-methylbutanoate:(R)-maconelliyl (S)-2-methylbutanoate is about 1:about 2 to about 1:about 10 (preferably about 1:about 5).

The above composition, wherein said composition contains a carrier material or carrier (e.g., an agronomically acceptable carrier).

A method for attracting male pink hibiscus mealybugs to an object or area (or locus), comprising (or consisting essentially of or consisting of) treating said object or area (or locus) with a male pink hibiscus mealybug attracting (synthetic) composition comprising (or consisting essentially of or consisting of) a male pink hibiscus mealybug attracting effective amount of (R)-lavandulyl (S)-2-methylbutanoate) and (R)-maconelliyl (S)-2-methylbutanoate, and optionally a carrier material or carrier (e.g., an agronomically acceptable carrier).

The above method, wherein the molar ratio of said (R)-lavandulyl (S)-2-methylbutanoate:(R)-maconelliyl (S)-2-methylbutanoate is about 1:about 2 to about 1:about 10 (preferably about 1:about 5).

The above method, wherein said composition contains a carrier material or carrier (e.g., an agronomically acceptable carrier).

A method of disrupting pink hibiscus mealybug mating, comprising (or consisting essentially of or consisting of) exposing a pink hibiscus mealybug population to a composition comprising (or consisting essentially of or consisting of) a pink hibiscus mealybug mating disrupting effective amount of (R)-lavandulyl (S)-2-methylbutanoate and (R)-maconelliyl (S)-2-methylbutanoate, and optionally a carrier material or carrier (e.g., an agronomically acceptable carrier).

The above method, wherein said composition contains a carrier material or carrier (e.g., an agronomically acceptable carrier).

A method for making [(R)-2,2-dimethyl-3-(1-methylethylidene)cyclobutyl]methyl (S)-2-methylbutanoate (2), said method comprising (or consisting essentially of or consisting of) reacting (1R,3S)-3-acetyl-2,2-dimethylcyclobutanecarboxylic acid [(cis)-pinononic acid] with methyl magnesium chloride to form (1R,3S)-3-(1-hydroxy-1-methylethyl)-2,2-dimethylcyclobutanecarboxylic acid (3) or reacting (1R,3S)-3-acetyl-2,2-dimethylcyclobutanecarboxylic acid [(cis)-pinononic acid] with methyl lithium, and then methyl magnesium chloride to form (1R,3S)-3-(1-hydroxy-1-methylethyl)-2,2-dimethylcyclobutanecarboxylic acid (3); reacting (1R,3S)-3-(1-hydroxy-1-methylethyl)-2,2-dimethylcyclobutanecarboxylic acid (3) with phosphorus oxychloride to form (1R,5S)-4,4,6,6-tetramethyl-3-oxabicyclo[3.1.1]heptan-2-one (4); reacting (1R,5S)-4,4,6,6-tetramethyl-3-oxabicyclo[3.1.1]heptan-2-one (4) with p-toluenesulfonic acid to form (R)-2,2-dimethyl-3-(1-methlethylidene)cyclobutanecarboxylic acid (5); reacting (R)-2,2-dimethyl-3-(1-methlethylidene)cyclobutanecarboxylic acid (5) with lithium aluminum hydride to form [(R)-(–)-2,2-dimethyl-3-(1-methylethylidene)cyclobutyl]methanol [(R)-maconelliol] (6), and reacting [(R)-(–)-2,2-dimethyl-3-(1-methylethylidene)cyclobutyl]methanol (6) with oxalyl chloride and (S)-2-methylbutanoic acid to form [(R)-2,2-dimethyl-3-(1-methylethylidene)cyclobutyl]methyl (S)-2-methylbutanoate [(R)-maconelliyl (S)-2-methylbutanoate] (2).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A composition consisting of at least one cyclobutane having the formula:

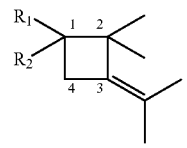

wherein $R_1$ is hydrogen, a $C_{1-11}$ straight or branched alcohol, aldehyde, alkyl, ether, or esters thereof with a $C_{1-10}$ saturated or unsaturated, straight or branched acid and $R_2$ is hydrogen, methyl, or $C_{2-10}$ saturated or unsaturated, straight or branched alkyl; an agronomically acceptable carrier material or carrier, and optionally (R)-lavandulyl (S)-2-methylbutanoate; wherein said cyclobutane is (R)-maconelliyl (S)-2-methylbutanoate.

2. A composition for attracting male pink hibiscus mealybugs, consisting of a male pink hibiscus mealybug attracting effective amount of (R)-lavandulyl (S)-2-methylbutanoate and (R)-maconelliyl (S)-2-methylbutanoate, and an agronomically acceptable carrier material or carrier.

3. The composition according to claim 2, wherein the molar ratio of said (R)-lavandulyl (S)-2-methylbutanoate:(R)-maconelliyl (S)-2-methylbutanoate is about 1:about 2 to about 1:about 10.

4. The composition according to claim 2, wherein the molar ratio of said (R)-lavandulyl (S)-2-methylbutanoate:(R)-maconelliyl (S)-2-methylbutanoate is about 1:about 5.

5. A method for attracting male pink hibiscus mealybugs to an object or area, comprising treating said object or area with a male pink hibiscus mealybug attracting composition comprising a male pink hibiscus mealybug attractant effective amount of (R)-lavandulyl (S)-2-methylbutanoate) and (R)-maconelliyl (S)-2-methylbutanoate, and optionally a carrier material or carrier.

6. The method according to claim 5, wherein the molar ratio of said (R)-lavandulyl (S)-2-methylbutanoate:(R)-maconelliyl (S)-2-methylbutanoate is about 1:about 2 to about 1:about 10.

7. The method according to claim 5, wherein the molar ratio of said (R)-lavandulyl (S)-2-methylbutanoate:(R)-maconelliyl (S)-2-methylbutanoate is about 1:about 5.

8. A method of disrupting pink hibiscus mealybug mating, comprising exposing a pink hibiscus mealybug population to a composition comprising a pink hibiscus mealybug mating disrupting effective amount of (R)-lavandulyl (S)-2-methylbutanoate and (R)-maconelliyl (S)-2-methylbutanoate, and optionally a carrier material or carrier.

9. A method for making [(R)-2,2-dimethyl-3-(1-methylethylidene)cyclobutyl]methyl (S)-2-methylbutanoate, said method comprising reacting (1R,3S)-3-acetyl-2,2-dimethylcyclobutanecarboxylic acid with methyl magnesium chloride to form (1R,3S)-3-(1-hydroxy-1-methylethyl)-2,2-dimethylcyclobutanecarboxylic acid or reacting (1R,3S)-3-acetyl-2,2-dimethylcyclobutanecarboxylic acid with methyl lithium, and then methyl magnesium chloride to form (1R,3S)-3-(1-hydroxy-1-methylethyl)-2,2-dimethylcyclobutanecarboxylic acid; reacting said (1R,3S)-3-(1-hydroxy-1-methylethyl)-2,2-dimethylcyclobutanecarboxylic acid with phosphorus oxychloride to form (1R,5S)-4,4,6,6-tetramethyl-3-oxabicyclo[3.1.1]heptan-2-one; reacting said (1R,5S)-4,4,6,6-tetramethyl-3-oxabicyclo[3.1.1]heptan-2-one with p-toluenesulfonic acid to form (R)-2,2-dimethyl-3-(1-methlethylidene)cyclobutanecarboxylic acid; reacting said (R)-2,2-dimethyl-3-(1-methlethylidene)cyclobutanecarboxylic acid with lithium aluminum hydride to form [(R)-(−)-2,2-dimethyl-3-(1-methylethylidene)cyclobutyl]methanol; and reacting said [(R)-(−)-2,2-dimethyl-3-(1-methylethylidene)cyclobutyl]methanol with oxalyl chloride and (S)-2-methylbutanoic acid to form [(R)-2,2-dimethyl-3-(1-methylethylidene)cyclobutyl]methyl (S)-2-methylbutanoate.

* * * * *